(12) United States Patent
Jacobs et al.

(10) Patent No.: US 7,951,372 B1
(45) Date of Patent: *May 31, 2011

(54) METHOD OF TREATING PSORIASIS BY ADMINISTERING IL-22 ANTIBODIES, OR BINDING FRAGMENTS THEREOF

(75) Inventors: Kenneth Jacobs, Newton, MA (US); Debra D. Pittman, Windham, NH (US); Lynette Fouser, Acton, MA (US); Vikki Spaulding, Lowell, MA (US); Dejun Xuan, Chestnut Hill, MA (US)

(73) Assignee: Wyeth LLC, Madison, NJ (US)

( * ) Notice: Subject to any disclaimer, the term of this patent is extended or adjusted under 35 U.S.C. 154(b) by 290 days.

This patent is subject to a terminal disclaimer.

(21) Appl. No.: 11/896,363

(22) Filed: Aug. 31, 2007

Related U.S. Application Data

(60) Division of application No. 10/256,977, filed on Sep. 27, 2002, now Pat. No. 7,279,559, which is a continuation of application No. 10/084,298, filed on Feb. 25, 2002, now Pat. No. 6,939,545, and a continuation-in-part of application No. 09/561,811, filed on Apr. 28, 2000, now Pat. No. 7,307,161.

(60) Provisional application No. 60/281,353, filed on Apr. 3, 2001, provisional application No. 60/270,823, filed on Feb. 23, 2001, provisional application No. 60/131,473, filed on Apr. 28, 1999.

(51) Int. Cl.
*A61K 39/395* (2006.01)
*A61K 39/00* (2006.01)

(52) U.S. Cl. ............... 424/139.1; 424/130.1; 424/133.1; 424/135.1; 424/141.1; 424/142.1; 424/145.1

(58) Field of Classification Search .................. None
See application file for complete search history.

(56) References Cited

U.S. PATENT DOCUMENTS

| 5,350,836 A | 9/1994 | Kopchick et al. |
| 5,536,637 A | 7/1996 | Jacobs |
| 5,674,487 A | 10/1997 | Smith et al. |
| 5,837,232 A | 11/1998 | DeWaal Malefyt et al. |
| 5,863,796 A | 1/1999 | Moore et al. |
| 6,143,867 A | 11/2000 | Akerblom |
| 6,225,117 B1 | 5/2001 | Gately et al. |
| 6,274,710 B1 | 8/2001 | Dumoutier et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 2001/0006637 A1 | 7/2001 | Akahoshi et al. |
| 2001/0023070 A1 | 9/2001 | Ebner et al. |
| 2001/0024652 A1 | 9/2001 | Dumoutier et al. |
| 2002/0012669 A1 | 1/2002 | Presnell et al. |
| 2002/0102723 A1 | 8/2002 | Gurney et al. |
| 2002/0177165 A1 | 11/2002 | Ashkenazi et al. |
| 2002/0187523 A1 | 12/2002 | Tang et al. |
| 2003/0003545 A1 | 1/2003 | Ebner et al. |
| 2003/0012788 A1 | 1/2003 | Renauld et al. |
| 2003/0092133 A1 | 5/2003 | Ebner et al. |
| 2003/0170823 A1 | 9/2003 | Presnell et al. |
| 2004/0023341 A1 | 2/2004 | Xu et al. |
| 2004/0110189 A1 | 6/2004 | Dumoutier et al. |
| 2004/0152125 A1 | 8/2004 | Presenell et al. |
| 2004/0180399 A1 | 9/2004 | Renauld et al. |
| 2005/0042220 A1 | 2/2005 | Li et al. |
| 2007/0196370 A1 * | 8/2007 | Fouser et al. ............. 424/144.1 |
| 2007/0258982 A1 | 11/2007 | Fouser et al. |

FOREIGN PATENT DOCUMENTS

| WO | WO 94/01548 A2 | 1/1994 |
| WO | WO 99/61617 | 12/1999 |
| WO | WO 00/24758 | 5/2000 |
| WO | WO 00/70049 | 11/2000 |
| WO | WO 00/73457 A1 | 12/2000 |
| WO | WO 00/77037 A2 | 12/2000 |
| WO | WO 01/46422 A1 | 6/2001 |
| WO | WO 02/10393 A2 | 2/2002 |
| WO | WO 02/16611 | 2/2002 |

OTHER PUBLICATIONS

Sugimoto et al. Gastroenterology: 2006: 130; 4: Suppl. 2: A41.
Sugimoto et al. Gastroenterology: 2005: 128: Suppl. 2: A18.
Van Deventer et al. Reaserach and Clinical Forums. 1998; 20; 11-18.
Andoh et al., "Interleukin-22, a member of the IL-10 subfamily, induces inflammatory responses in colonic subepithelial myofibroblasts", Gastroenterology: 2005 129:969-84.
Brand et al. Am. J. Physiol. Gastrointest. Liver Physiol.: 2006: 290:G827-38.
Sugimoto et al., "IL-22 Ameliorates intestinal inmflammation in a mouse model of ulcerative colitis", The Journal of Clinical Investigation: 2008: 118:534-44.
Carvahlo et al., Inflamm Bowel Dis. 2008; 14:1051-60.
Dumoutier et al., Absence of IL-22 aggravates dextran-sulfate [DSS] induced colitis; Abstract #42, Cytokine 43 (2008) 243-262.
Ouyang et al., Mucosal Immunology, 2008; 1:335-338.
Wolk et al., J Immunol. 2007; 178:5973-81.
Schmechel et al., Inflamm Bowel Dis. 2008; 14: 204-12.
Mahairas, G. et al., Database EST. Accession No. AQ104025. Aug. 28, 1998.
Waterston, R. et al., Database GenEmbl. Accession No. AC006734. Feb. 25, 1999.
Wilson, R. et al., J. Mol. Biol. 261:155-172, 1996.
Bork, et al., Trends in Genetics, 12:425-427, 1996.
Vukicevic, et al., PNAS USA 93:9021-9026, 1996. Massague, J. Cell, 49:437-8, 1987.
Pilbeam, et al., Bone 14:717-720, 1993.
Skolnick, et al., Trends in Biotech. 18:34-39, 2000.
Dumoutier, et al. (2000), "Cloning and characterization of IL-10-related T cell-derived inducible factor (IL-TIF), a novel cytokine structurally related to IL-10 and inducible by IL-9," J. of Immunol. 164:1814-1819.
Syrbe, et al. (1999) Springer Seminars in Immunopathology, 21:263-85.
Dumoutier, L. et al., GenBank Accession No. NM_016971 for *mus musculus* interleukin 10-related T cell-derived inducible factor (Iltif). Jun. 8, 2000.
Aoki, I., et al. "Comparison of the amino acid and nucleotide sequences between human and two guinea pig major basic proteins," FEBS Lett. 282(1):56-60, 1991.

(Continued)

*Primary Examiner* — Robert Landsman

(57) ABSTRACT

Inhibitors of IL-22 are disclosed as well as pharmaceutical compositions and methods of using same. The inhibitors include IL-22 antibodies and are useful for treating inflammatory disorders.

24 Claims, 5 Drawing Sheets

OTHER PUBLICATIONS

Dumoutier, L. et al., "Human interleukin-10-related T cell-derived inducible factor: molecular cloning and functional characterization as an hepatocyte-stimulating factor," PNAS 97(18):10144-9, 2000.

Dumoutier, L. et al., "IL-TIF-/IL-22: genomic organization and mapping of the human and mouse genes," Genes Immun. 1:488-494, 2000.

Ozaki, T. et al., GenBank Accession No. D13973 for *Dictyostelium discoideum* DNA for Dp87 protein, 1993. Feb. 1, 2000.

Aoki, I. et al., GenBank Accession No. P35709 for *Eosinophil* granule major basic protein 2 percursor (mbp-2). May 30, 2000.

Xie, M. et al. GenBank Accession No. AF279437 for *Homo sapiens* interleukin 22 (IL22). Oct. 9, 2000.

Dumoutier, L. et al., GenBank Accession No. AJ294727 for *Mus musculus* ILTIFa gene for IL TIE alpha protein (IL-22), exons 1a 5. Dec. 21, 2000.

Dumoutier, L. et al., GenBank Accession No. NP_065386 for Interleukin 22: IL-10 related T-cell derived inducible factor (*Homo sapiens*). Nov. 2, 2000.

Ozaki, T. et al., "Developmental regulation of transcription of a novel prespore-specific gene (Dp87) in *Dictyostelium discoideum*," Development. 117(4):1299-308, 1993.

Sambrook, J. et al., Molecular Cloning. A Laboratory Manual, 2d ed. Cold Spring Harbor Laboratory Press, 1989, Ch. 17.

Xie, M.H. et al., "Interleukin IL-22, a novel human cytokine that signals through the interferon receptor-related proteins CRF2-4 and IL-22R," J. Biol. Chem. 275(40):31335-9, 2000.

Dumoutier, L. et al, "Cloning and Characterization of IL-10-Related T Cell-Derived Inducible Factor (IL-TIF), A Novel Cytokine Structurally Related to IL-10 and Inducible by IL-9" Journal of Immunology, Blackwell Scientific Publications, GB, vol. 164-, 2000, pp. 1814-1819.

Dumoutier, L. et al., "Human Interleukin-10-Related T Cell-Derived Inducible Factor: Molecular Cloning and Functional Characterization as an Hepatocyte-Stimulating Factor" Proceedings of the National Academy of Sciences of USA, National Academy of Science. Washington, US, vol. 97, No. 18, Aug. 29, 2000, pp. 10144-10149.

Xie, M-H et al., "Interleukin (IL)-22, a novel human cytokine that signals through the interferon receptor-related proteins CRF2-4 and IL-22R" Journal of Biological Chemistry, American Society of Biological Chemists, Baltimore, MD US, vol. 275, No. 40, Oct. 6, 2000, pp. 31335-31339.

Kotenko, Sergei V. et al., "Identification of the functional interleukin-22 (IL-22) receptor complex. The IL-10R2 chain (IL-10Rbeta) is a common chain of both the IL-10 and IL-22 (IL-10-related T cell-derived inducible factor, IL-TIF) receptor complexes" Journal of Biological Chemistry, American Society of Biological chemists, Baltimore, MD, US, vol. 276, No. 4, Jan. 26, 2001, pp. 2725-2732.

Dumoutier, L. et al., "IL-TIF induces acute phase reactant production by hepatocytes through IL-10Rbeta." Immunology Letters, vol. 73, No. 2-3 Sep. 2000, p. 261.

Lambert, A. et al., "Novel cytokine IL-22 administered by adenovirus vector or as recombinant purified protein induces acute-phase responses and renal tubular basophilia in female C57BL/6 mice." Toxicologic Pathology, vol. 29, No. 6, Nov. 2001, p. 712.

Bork, P., Genome Research 10:398-400, 2000.

Doerks et al., Trends in Genetics 14:248-250, 1998.

Smith et al., Nature Biotechnology 15:1222-1223, 1997.

Brenner, S.E., Trends in Genetics, 15:132-133, 1999.

Mahairas, et al., PNAS, USA, 96(17) 9739-9744 (1999).

Simon L.S., et al. (Jun. 2000), New and future drug therapies for rheumatoid arthritis, Rheumatology 39:36-42.

Liorente L., et al. (2000), Clinical and Biological Effects of Anti-Interleukin-10 Monoclonal Antibody Administration in Systemic Lupus Erythematosus, Arthritis & Rheumatism 43(8):1790-1800.

Van den Bert W. (1998), Joint inflammation and cartilage destruction may occur uncoupled, Springer Semin Immunopathol. 20:149-164.

R&D Systems, Catalog NR, AF582, XP002307633, "Anti-Mouse IL-22 Antibody," Aug. 22, 2002.

Kotenko, Sergei, "The Family of IL-10-Related Cytokines and receptors: Related, But to What Extent?", Cytokine and Growth Factor Reviews, vol. 13, No. 3, Jun. 2002, pp. 223-240.

Radaeva, Svetlana, et al., "Interleukin 22 (IL-22) Plays a Protective Role in T Cell-Mediated Murine Hepatitis: IL-22 is a Survival Factor for Hepatocytes via STAT3 Activation," Hepatology, vol. 39, No. 5, May 2004, pp. 1332-1342.

Resmini, Christine, et al., "An Anti-Murine IL-22 Monoclonal Antibody Decreases Disease Severity in a Murine Model of Collagen Induced Arthritis," European Cytokine Network, vol. 14, No. Supplement 3, Sep. 2003, p. 129 and Annual Meeting of the International Cytokine Society; Dublin, Ireland, Sep. 20-24, 2003, ISSN: 1448-5493.

Li, J. et al., "Temporal Associations Between Interleukin 22 and the Extracellular Domains of IL-22R and IL-10R2," International Immunopharmacology, Elsevier, Amsterdam, NL, vol. 4, No. 5, May 2004, pp. 693-708.

Smith et al., (JEM, 2009; 206: 1883-1897).

* cited by examiner

SEQUENCE LISTING

```
<160> NUMBER OF SEQ ID NOS: 10

<210> SEQ ID NO 1
<211> LENGTH: 1191
<212> TYPE: DNA
<213> ORGANISM: Homo sapiens

<400> SEQUENCE: 1
gaattcggcc aaagaggcct acaggttctc cttccccagt caccagttgc tcgagttaga      60
attgtctgca atggccgccc tgcagaaatc tgtgagctct ttccttatgg ggaccctggc     120
caccagctgc ctccttctct tggccctctt ggtacaggga ggagcagctg cgcccatcag     180
ctcccactgc aggcttgaca agtccaactt ccagcagccc tatatcacca accgcacctt     240
catgctggct aaggaggcta gcttggctga taacaacaca gacgttcgtc tcattgggga     300
gaaactgttc cacggagtca gtatgagtga gcgctgctat ctgatgaagc aggtgctgaa     360
cttcacccct gaagaagtgc tgttccctca atctgatagg ttccagcctt atatgcagga     420
ggtggtgccc ttcctggcca ggctcagcaa caggctaagc acatgtcata ttgaaggtga     480
tgacctgcat atccagagga atgtgcaaaa gctgaaggac acagtgaaaa agcttggaga     540
gagtggagag atcaaagcaa ttggagaact ggatttgctg tttatgtctc tgagaaatgc     600
ctgcatttga ccagagcaaa gctgaaaaat gaataactaa ccccctttcc ctgctagaaa     660
taacaattag atgccccaaa gcgatttttt ttaaccaaaa ggaagatggg aagccaaact     720
ccatcatgat gggtggattc caaatgaacc cctgcgttag ttacaaagga accaatgcc     780 acttttgttt ataagaccag aaggtagact ttctaagcat agatatttat tgataacatt     840
tcattgtaac tggtgttcta tacacagaaa acaatttatt ttttaaataa ttgtcttttt     900
ccataaaaaa gattactttc cattcctta ggggaaaaaa cccctaaata gcttcatgtt     960
tccataatca gtactttata tttataaatg tatttattat tattataaga ctgcatttta    1020
tttatatcat tttattaata tggatttatt tatagaaaca tcattcgata ttgctacttg    1080
agtgtaaggc taatattgat atttatgaca ataattatag agctataaca tgtttatttg    1140
acctcaataa acacttggat atcctaaaaa aaaaaaaaaa aaagcggccg c             1191

<210> SEQ ID NO 2
<211> LENGTH: 179
<212> TYPE: PRT
<213> ORGANISM: Homo sapiens

<400> SEQUENCE: 2

Met Ala Ala Leu Gln Lys Ser Val Ser Ser Phe Leu Met Gly Thr Leu
  1               5                  10                  15

Ala Thr Ser Cys Leu Leu Leu Leu Ala Leu Leu Val Gln Gly Gly Ala
             20                  25                  30

Ala Ala Pro Ile Ser Ser His Cys Arg Leu Asp Lys Ser Asn Phe Gln
         35                  40                  45

Gln Pro Tyr Ile Thr Asn Arg Thr Phe Met Leu Ala Lys Glu Ala Ser
```

```
                50                  55                  60
Leu Ala Asp Asn Asn Thr Asp Val Arg Leu Ile Gly Glu Lys Leu Phe
 65                  70                  75                  80

His Gly Val Ser Met Ser Glu Arg Cys Tyr Leu Met Lys Gln Val Leu
                 85                  90                  95

Asn Phe Thr Leu Glu Glu Val Leu Phe Pro Gln Ser Asp Arg Phe Gln
             100                 105                 110

Pro Tyr Met Gln Glu Val Val Pro Phe Leu Ala Arg Leu Ser Asn Arg
         115                 120                 125

Leu Ser Thr Cys His Ile Glu Gly Asp Asp Leu His Ile Gln Arg Asn
     130                 135                 140

Val Gln Lys Leu Lys Asp Thr Val Lys Lys Leu Gly Glu Ser Gly Glu
 145                 150                 155                 160

Ile Lys Ala Ile Gly Glu Leu Asp Leu Leu Phe Met Ser Leu Arg Asn
                 165                 170                 175

Ala Cys Ile

<210> SEQ ID NO 3
<211> LENGTH: 1166
<212> TYPE: DNA
<213> ORGANISM: Murine

<400> SEQUENCE: 3
gaattcggcc aaagaggcct acctaaacag gctctcctct cagttatcaa ctgttgacac      60
ttgtgcgatc tctgatggct gtcctgcaga atctatgag tttttccctt atggggactt     120
tggccgccag ctgcctgctt ctcattgccc tgtgggccca ggaggcaaat gcgctgcccg     180
tcaacacccg gtgcaagctt gaggtgtcca acttccagca gccatacatc gtcaaccgca     240
cctttatgct ggccaaggag gccagccttg cagataacaa cacagatgtc cggctcatcg     300
gggagaaact gttccgagga gtcagtgcta aggatcagtg ctacctgatg aagcaggtgc     360
tcaacttcac cctggaagac gttctgctcc cccagtcaga caggttccag ccctacatgc     420
aggaggtggt gccttttcctg accaaactca gcaatcagct cagctcctgt cacatcagcg     480
gtgacgacca gaacatccag aagaatgtca aaggctgaa ggagacagtg aaaaagcttg     540
gagagagtgg agagatcaag gcgattgggg aactggacct gctgtttatg tctctgagaa     600
atgcttgcgt ctgagcgaga agaagctaga aacgaagaa ctgctccttc ctgccttcta     660
aaaagaacaa taagatcccct gaatggactt ttttactaaa ggaaagtgag aagctaacgt     720
ccatcattat tagaagattt cacatgaaac ctggctcagt tgaaaagaa aatagtgtca     780 agttgtccat gagaccagag gtagacttga taaccacaaa gattcattga caatatttta     840
ttgtcactga tgatacaaca gaaaaataat gtactttaaa aaattgtttg aaaggaggtt     900
acctctcatt cctttagaaa aaaagctta gtaacttcat ttccataacc aatatttat      960 atatgtaagt ttatttata taagtataca ttttatttat gtcagtttat taatatggat     1020 ttattttatag aaacattatc tgctattgat atttagtata aggcaaataa tatttatgac     1080
aataactatg gaaacaagat atcttaggct ttaataaaca catggatatc ataaaaaaaaa     1140 aaaaaaaaaa aaaaaaagc ggccgc                                          1166

<210> SEQ ID NO 4
<211> LENGTH: 180
<212> TYPE: PRT
<213> ORGANISM: Murine
<220> FEATURE:
<221> NAME/KEY: VARIANT
```

```
<222> LOCATION: (180)
<223> OTHER INFORMATION: Wherein Xaa is any amino acid.

<400> SEQUENCE: 4

Met Ala Val Leu Gln Lys Ser Met Ser Phe Ser Leu Met Gly Thr Leu
 1               5                  10                  15

Ala Ala Ser Cys Leu Leu Leu Ile Ala Leu Trp Ala Gln Glu Ala Asn
                20                  25                  30

Ala Leu Pro Val Asn Thr Arg Cys Lys Leu Glu Val Ser Asn Phe Gln
            35                  40                  45

Gln Pro Tyr Ile Val Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val Xaa
            180

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide for generation of sense probe

<400> SEQUENCE: 5
aggatggaga catctgactg ccctacg                                          27

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide for the generation of sense probe.

<400> SEQUENCE: 6
gactgataat acgactcact atagggcgaa caattttgac tccgatattg tccaag          56

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide for generation of anti-sense probe

<400> SEQUENCE: 7
acaattttga ctccgatatt gtccaag                                          27
```

```
<210> SEQ ID NO 8
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide for generation of anti-sense probe

<400> SEQUENCE: 8
gactgataat acgactcact atagggcgaa ggatggagac atctgactgc cctacg         56

<210> SEQ ID NO 9
<211> LENGTH: 191
<212> TYPE: DNA
<213> ORGANISM: Artificial Sequence
<220> FEATURE:
<223> OTHER INFORMATION: Description of Artificial Sequence: Probe for
      IL-22 sequences

<400> SEQUENCE: 9
cagccataca tcgtcaaccg caccttatg ctggccaagg aggccagcct tgcagataac         60
aacacagatg tccggctcat cggggagaaa ctgttccgag gagtcagtgc taaggatcag        120
tgctacctga tgaagcaggt gctcaacttc accctggaag acgttctgct cccccagtca        180
gacaggttcc a                                                             191

<210> SEQ ID NO 10
<211> LENGTH: 49
<212> TYPE: PRT
<213> ORGANISM: Artificial Sequence
<220> FEATURE:
<223> OTHER INFORMATION: Description of Artificial Sequence: Amino acid
      tag

<400> SEQUENCE: 10

Met Lys Phe Leu Val Asn Val Ala Leu Val Phe Met Val Val Tyr Ile
 1               5                  10                  15

Ser Tyr Ile Tyr Ala Gly Ser Gly His His His His His His Gly Ser
             20                  25                  30

Gly Asp Tyr Lys Asp Asp Asp Asp Lys Ala Pro Ile Ser Ser His Cys
         35                  40                  45

Arg
```

US 7,951,372 B1

METHOD OF TREATING PSORIASIS BY ADMINISTERING IL-22 ANTIBODIES, OR BINDING FRAGMENTS THEREOF

CROSS-REFERENCE TO RELATED APPLICATIONS

This application is a divisional of U.S. application Ser. No. 10/256,977 (now U.S. Pat. No. 7,279,559), filed Sep. 27, 2002, which is a continuation of application Ser. No. 10/084, 298, filed Feb. 25, 2002 (now U.S. Pat. No. 6,939,545), which claims priority to application No. 60/270,823, filed Feb. 23, 2001, and application No. 60/281,353, filed Apr. 3, 2001; and which is a continuation-in-part of application Ser. No. 09/561,811 (now U.S. Pat. No. 7,307,161), filed Apr. 28, 2000, which claims the benefit of application No. 60/131,473, filed Apr. 28, 1999. The contents of all these application are hereby incorporated by reference in their entirety.

FIELD OF THE INVENTION

The invention is related to cytokine polypeptides and polynucleotides encoding these polypeptides. The invention is also related to antibodies to cytokine polypeptides and to therapeutic compositions that include these antibodies. The compositions are useful in treating, e.g., inflammatory states such as arthritis.

BACKGROUND OF THE INVENTION

Inflammatory arthritis represents is a family of arthritic diseases characterized by lymphokine-mediated inflammation of the joints. Inflammatory arthritis is often autoimmune in origin. Examples of inflammatory arthritis can include rheumatoid arthritis, psoriatic arthritis, and lupus-associated arthritis. The most common form of inflammatory arthritis is rheumatoid arthritis. Rheumatoid arthritis, is characterized by persistent inflammation of the joints. Inflammation can eventually lead to cartilage destruction and bone erosion.

SUMMARY OF THE INVENTION

The invention is based in part on the discovery that inhibitors of the cytokine IL-22 can inhibit symptoms associated with arthritis. More particularly, antibodies raised against IL-22 (which is also referred to herein as GIL-19 and AE289) have been found to inhibit the development of symptoms associated with collagen-induced arthritis in a murine model system.

In one aspect, the invention features an antibody which immunologically reacts with an IL 22 protein. The antibody can be, e.g., a neutralizing antibody. In preferred embodiments, the antibody is a monoclonal antibody. Examples of monoclonal antibodies include a human monoclonal antibody and a humanized monoclonal antibody.

In some embodiments, the antibody binds specifically to a polypeptide that includes the amino acid sequence of SEQ ID NO:2, which corresponds to the amino acid sequence of a human. IL-22 polypeptide.

Also provided by the invention is a pharmaceutical composition comprising an IL-22 antibody which immunologically reacts with an IL 22 protein comprising the amino acid sequence of SEQ ID NO:2 and a pharmaceutical carrier. The antibody in the pharmaceutical composition is preferably a neutralizing antibody. The antibody is preferably a monoclonal antibody, such as a human monoclonal antibody or a humanized monoclonal antibody.

Also provided by the invention is a method of treating a pathological condition in a subject associated with IL-22 activity by administering an effective amount of an agent that inhibits levels of IL-22 activity, thereby treating the pathological condition.

The pathological condition can be, e.g., septicemia, and autoimmune disorders. Suitable autoimmune disorders include, e.g., rheumatoid arthritis, osteoarthritis, multiple sclerosis, myasthenia gravis, inflammatory bowel disease, lupus, diabetes and psoriasis. These responses can be associated wound healing processes, cholesterol metabolism, oxygen free radical injury, ischemia, atherosclerosis and allergies.

Also provided by the invention is a method of treating symptoms associated with arthritis, the method by administering to a subject in need thereof a therapeutically effective amount of an IL-22 antibody. In some embodiments, the arthritis is rheumatoid arthritis.

The IL-22 antibody can be administered therapeutically or prophylactically, or both.

Also provided by the invention is a method of enhancing a subject's immune response to an antigen by administering to the subject an immunogenic amount of the antigen and an immunogenicity-augmenting amount of IL-22 in concurrent or sequential combination with the antigen such that the subject's immune response is enhanced.

Also provided is a method of treating a pathological condition in a subject in need of IL-22 modulation by administering an effective amount of an agent that modulates IL-22 activity, such that the pathological condition in the subject is treated.

The work described herein reveals that IL-22 is a cytokine involved in acute phase responses. The invention provides for the use of IL-22 as well as IL-22 modulatory agents (i.e., agents that stimulate or inhibit IL-22 activity) to alter an immune response, either through its upregulation or downregulation, depending on the clinical situation.

As used herein, the term "IL-22" molecule includes nucleic acid molecules, proteins, polypeptides, and fragments or variants thereof having at least one IL-22 activity as defined herein. In a preferred embodiment, the IL-22 molecule is a human IL-22 molecule (e.g. the human IL-22 nucleic acid and protein molecules set forth in SEQ ID NO: 1 and SEQ ID NO:2).

In one embodiment, the present invention provides a composition comprising an isolated polynucleotide selected from the group consisting of:
  (a) a polynucleotide comprising the nucleotide sequence of SEQ ID NO:1;
  (b) a polynucleotide comprising the nucleotide sequence of SEQ ID NO:1 from nucleotide 65 to nucleotide 601;
  (c) a polynucleotide comprising the nucleotide sequence of the full-length protein coding sequence of clone IL-22 deposited under accession number ATCC 207231;
  (d) a polynucleotide encoding the full-length protein encoded by the cDNA insert of clone IL-22 deposited under accession number ATCC 207231;
  (e) a polynucleotide comprising the nucleotide sequence of a mature protein coding sequence of clone IL-22 deposited under accession number ATCC 207231;
  (f) a polynucleotide encoding a mature protein encoded by the cDNA insert of clone IL-22 deposited under accession number ATCC 207231;
  (g) a polynucleotide encoding a protein comprising the amino acid sequence of SEQ ID NO:2;
  (h) a polynucleotide encoding a protein comprising a fragment of the amino acid sequence of SEQ ID NO:2 having biological activity, the fragment comprising eight contiguous amino acids of SEQ ID NO:2;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and a polynucleotide that hybridizes under stringent conditions to any one of the polynucleotides specified in (a)-(h) and that has a length that is at least 25% of the length of SEQ ID NO:1.

Preferably, such polynucleotide comprises the nucleotide sequence of SEQ ID NO:1 from nucleotide 65 to nucleotide 601; the nucleotide sequence of the full-length protein coding sequence of clone IL-22 deposited under accession number ATCC 207231; or the nucleotide sequence of a mature protein coding sequence of clone IL-22 deposited under accession number ATCC 207231 (e.g., nucleotides 1-1177 of SEQ ID NO:1). In other preferred embodiments, the polynucleotide encodes the full-length or a mature protein encoded by the cDNA insert of clone IL-22 deposited under accession number ATCC 207231 (e.g., amino acids 1-179 of SEQ ID NO: 2). In further preferred embodiments, the present invention provides a polynucleotide encoding a protein comprising a fragment of the amino acid sequence of SEQ ID NO:2 having biological activity, the fragment preferably comprising eight (more preferably twenty, most preferably thirty) contiguous amino acids of SEQ ID NO:2, or a polynucleotide encoding a protein comprising a fragment of the amino acid sequence of SEQ ID NO:2 having biological activity, the fragment comprising the amino acid sequence from amino acid 84 to amino acid 93 of SEQ ID NO:2.

Other embodiments provide the gene corresponding to the cDNA sequence of SEQ ID NO:1.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:1, but excluding the poly(A) tail at the 3' end of SEQ ID NO:1; and
    (ab) the nucleotide sequence of the cDNA insert of clone IL-22 deposited under accession number ATCC 207231;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:1, but excluding the poly(A) tail at the 3' end of SEQ ID NO:1; and
    (bb) the nucleotide sequence of the cDNA insert of clone IL-22 deposited under accession number ATCC 207231;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:1, and extending contiguously from a nucleotide sequence corresponding to the 5' end of SEQ ID NO: 1 to a nucleotide sequence corresponding to the 3' end of SEQ ID NO:1, but excluding the poly(A) tail at the 3' end of SEQ ID NO:1. Also preferably the polynucleotide isolated according to the above process comprises a nucleotide sequence corresponding to the cDNA sequence of SEQ ID NO:1 from nucleotide 65 to nucleotide 601, and extending contiguously from a nucleotide sequence corresponding to the 5' end of said sequence of SEQ ID NO:1 from nucleotide 65 to nucleotide 601, to a nucleotide sequence corresponding to the 3' end of said sequence of SEQ ID NO: 1 from nucleotide 65 to nucleotide 601.

In other embodiments, the present invention provides a composition comprising a protein, wherein said protein comprises an amino acid sequence selected from the group consisting of:
  (a) the amino acid sequence of SEQ ID NO:2;
  (b) a fragment of the amino acid sequence of SEQ ID NO:2, the fragment comprising eight contiguous amino acids of SEQ ID NO:2; and
  (c) the amino acid sequence encoded by the cDNA insert of clone IL-22 deposited under accession number ATCC 207231;
the protein being substantially free from other mammalian proteins. Preferably such protein comprises the amino acid sequence of SEQ ID NO:2. In further preferred embodiments, the present invention provides a protein comprising a fragment of the amino acid sequence of SEQ ID NO:2 having biological activity, the fragment preferably comprising eight (more preferably twenty, most preferably thirty) contiguous amino acids of SEQ ID NO:2.

In certain preferred embodiments, the polynucleotide is operably linked to an expression control sequence. The invention also provides a host cell, including bacterial, yeast, insect and mammalian cells, transformed with such polynucleotide compositions. Also provided by the present invention are organisms that have enhanced, reduced, or modified expression of the gene(s) corresponding to the polynucleotide sequences disclosed herein.

Processes are also provided for producing a protein, which comprise:
  (a) growing a culture of the host cell transformed with such polynucleotide compositions in a suitable culture medium; and
  (b) purifying the protein from the culture.
The protein produced according to such methods is also provided by the present invention.

Protein compositions of the present invention may further comprise a pharmaceutically acceptable carrier. Compositions comprising an antibody which specifically reacts with such protein are also provided by the present invention.

As used herein, a "modulator", "agent" or "modulating agent" includes any proteins, polypeptides, nucleic acids, agonists or antagonists or protein, polypeptide or nucleic acid fragments or variants thereof that are capable of altering the activity of IL-22. For example, such altering of IL-22 activity may include the blocking of IL-22 activity, down-regulation of IL-22 activity or inhibition of IL-22 activity. Alternatively, the alteration of IL-22 activity may include the augmenting of IL-22 activity, the up-regulation of IL-22 activity or the enhancing of IL-22 activity.

In another embodiment, modulators that act on the present invention are provided. In a preferred embodiment, polyclonal and/or monoclonal antibodies of the present invention (e.g. neutralizing antibody specific for IL-22) are also provided to down-modulate an immune responses (i.e. to treat sepsis and other chronic inflammatory disorders). In another preferred embodiment, the present invention is used as a vaccine adjuvant to alter the type of immune response achieved by antigen alone.

In another embodiment, a method of treating a pathological condition in a subject is provided by modulating the activity of IL-22, such that the pathological condition is treated. In a preferred embodiment, the pathological condition treated is an infectious disease. More preferably, the infectious disease can be initiated by a bacteria, virus, parasite or fungi. In another preferred embodiment, the pathological condition is cancer, more preferably renal cell carcinoma.

In another embodiment, modulatory agents are used to alter inflammatory pathologies in the kidney, such as the induction of renal proximal tubular basophilia.

In another embodiment, the present invention will be used for the remodeling of tissues, both in vivo and ex vivo. In a preferred embodiment, IL-22, or agonists of IL-22 is used in the remodeling of epithelial tissue in the kidney.

In another embodiment, a method is provided for studying a disease in a subject comprising administering an agent that modulates the activity of IL-22 in vivo, such that the disease can be studied. In a preferred embodiment, the subject under study is a genetically altered mammal, preferably a genetically altered mouse, most preferably a transgenic or gene knock-out mouse.

Methods are also provided for preventing, treating or ameliorating a medical condition which comprises administering to a mammalian subject a therapeutically effective amount of a composition comprising a protein of the present invention and a pharmaceutically acceptable carrier.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION

Figure 1:
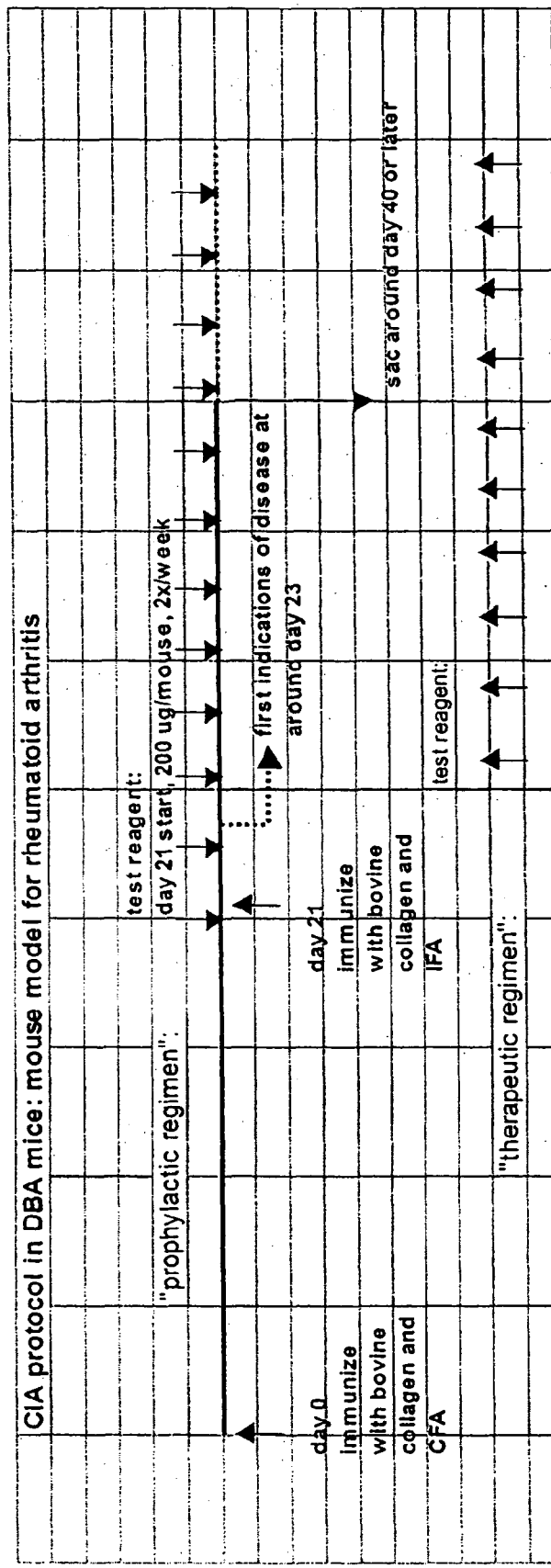
FIG. 1 is a schematic drawing showing an experimental protocol used to analyze the effect of an IL-22 antibody on an in vivo murine arthritis model.

The invention provides inhibitors of IL-22 and therapeutic compositions that include the antibodies. The inhibitors are useful for treating inflammatory states, which include, e.g., autoimmune diseases such as rheumatoid arthritis.

Inhibitors can be prepared using IL-22 polypeptide sequences and nucleic acids encoding same. IL-22 is produced by activated human and mouse Th1, but not Th2, CD4$^+$ cells. The cytokine is a multifunctional molecule whose expression is stimulated by LPS, but not IFN-γ. IL-22 shares approximately 20% homology with IL-10 and is produced by activated human and mouse Th1, but not Th2, CD4$^+$ cells. Furthermore, LPS; but not IFN-γ, strongly stimulates IL-22 production from the adherent cell compartment of murine PECs, indicating that IL-22 is involved in mediating natural immunity.

The addition of either an adenovirus encoding murine IL-22 or recombinant purified murine IL-22 intravenously injected into C57b/6 mice induced numerous systemic effects, including decreased red blood cell count, increased platelet count, decreased serum albumin, increased serum amyloid A and fibrinogen levels, and decreased body weight, all suggestive of an acute phase reaction. Moreover, IL-22 administration also induces basophilia in the proximal renal tubules, a finding distinct from an acute phase reaction, suggestive of induced cellular proliferation. Identification of these biological activities of IL-22 has led to the development of new approaches to and therapeutics useful for the treatment of various immune response-related diseases and disorders. Moreover, the role of IL-22 in processes including sepsis, chronic inflammation, and autoimmunity has been analyzed and new mechanisms for treating such conditions is disclosed herein.

I. Isolated IL-22 Proteins and Polynucleotides

IL-22 nucleotide and amino acid sequences are provided below. The nucleotide sequence of each clone can also be determined by sequencing of the deposited clone in accordance with known methods. The predicted amino acid sequence (both full-length and mature forms) can then be determined from such nucleotide sequence. The amino acid sequence of the protein encoded by a particular clone can also be determined by expression of the clone in a suitable host cell, collecting the protein and determining its sequence.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

A polynucleotide of the present invention has been identified initially as clone "hTIF/AE289", later renamed and referred to herein also as "IL-22." Clone IL-22 was isolated according to the following method. A murine EST was identified from a murine cDNA library made from splenocytes activated with both ConA and bone marrow derived dendritic cells. The EST was identified using methods which are selective for cDNAs encoding secreted proteins (see U.S. Pat. No. 5,536,637). The murine EST sequence was used to isolate a full-length murine clone from the same cDNA library (SEQ ID NO:3, shown below). Analysis of the sequence of the murine clone revealed a significant homology to interleukin-10 (IL-10).

In order to isolate a human homolog of the murine clone, PCR primers were constructed based upon the region of the murine sequence which showed homology to IL-10. Use of such primers for amplification in cDNA library derived from PHA/PMA stimulated human PBMCs produced a PCR product of significant size. Analysis of the sequence of the PCR product confirmed that it was a homolog of the murine cDNA. Oligonucleotides were constructed from the sequence of the partial human clone and used to isolate a full-length human clone from the PBMC library.

The disclosed human IL-22 nucleotide sequence is a full-length clone, including the entire coding sequence of a secreted protein. Analysis of its sequence confirms its homology to IL-10 at a level of 20%.

The nucleotide sequence of the disclosed human IL-22 polynucleotide sequence is reported below (SEQ ID NO:1), and includes a poly(A) tail. The disclosed nucleotide sequence includes an open reading frame and the amino acid sequence of full-length IL-22 protein corresponding to the foregoing nucleotide sequence is reported in SEQ ID NO:2. The amino acid sequence of mature IL-22 corresponds to amino acids 34-179 of SEQ ID NO: 2.
```
   1  GAATTCGGCC AAAGAGGCCT ACAGGTTCTC CTTCCCCAGT CACCAGTTGC
  51  TCGAGTTAGA ATTGTCTGCA ATGGCCGCCC TGCAGAAATC TGTGAGCTCT
 101  TTCCTTATGG GGACCCTGGC CACCAGCTGC CTCCTTCTCT TGGCCCTCTT
 151  GGTACAGGGA GGAGCAGCTG CGCCCATCAG CTCCCACTGC AGGCTTGACA
 201  AGTCCAACTT CCAGCAGCCC TATATCACCA ACCGCACCTT CATGCTGGCT
 251  AAGGAGGCTA GCTTGGCTGA TAACAACACA GACGTTCGTC TCATTGGGGA
 301  GAAACTGTTC CACGGAGTCA GTATGAGTGA GCGCTGCTAT CTGATGAAGC
 351  AGGTGCTGAA CTTCACCCTT GAAGAAGTGC TGTTCCCTCA ATCTGATAGG
 401  TTCCAGCCTT ATATGCAGGA GGTGGTGCCC TTCCTGGCCA GGCTCAGCAA
 451  CAGGCTAAGC ACATGTCATA TTGAAGGTGA TGACCTGCAT ATCCAGAGGA
 501  ATGTGCAAAA GCTGAAGGAC ACAGTGAAAA AGCTTGGAGA GAGTGGAGAG
 551  ATCAAAGCAA TTGGAGAACT GGATTTGCTG TTTATGTCTC TGAGAAATGC
 601  CTGCATTTGA CCAGAGCAAA GCTGAAAAAT GAATAACTAA CCCCCTTTCC
 651  CTGCTAGAAA TAACAATTAG ATGCCCCAAA GCGATTTTTT TTAACCAAAA
 701  GGAAGATGGG AAGCCAAACT CCATCATGAT GGGTGGATTC CAAATGAACC
 751  CCTGCGTTAG TTACAAAGGA AACCAATGCC ACTTTTGTTT ATAAGACCAG
 801  AAGGTAGACT TTCTAAGCAT AGATATTTAT TGATAACATT TCATTGTAAC
 851  TGGTGTTCTA TACACAGAAA ACAATTTATT TTTTAAATAA TTGTCTTTTT
 901  CCATAAAAAA GATTACTTTC CATTCCTTTA GGGGAAAAAA CCCCTAAATA
 951  GCTTCATGTT TCCATAATCA GTACTTTATA TTTATAAATG TATTTATTAT
1001  TATTATAAGA CTGCATTTTA TTTATATCAT TTTATTAATA TGGATTTATT
1051  TATAGAAACA TCATTCGATA TTGCTACTTG AGTGTAAGGC TAATATTGAT
1101  ATTTATGACA ATAATTATAG AGCTATAACA TGTTTATTTG ACCTCAATAA
1151  ACACTTGGAT ATCCTAAAAA AAAAAAAAAA AAAGCGGCCG C (SEQ ID NO: 1)
```

The polypeptide sequence of the encoded polypeptide is shown below.
  1 MAALQKSVSS FLMGTLATSC LLLLALLVQG GAAAPISSHC RLDKSNFQQP
 51 YITNRTFMLA KEASLADNNT DVRLIGEKLF HGVSMSERCY LMKQVLNFTL 101 EEVLFPQSDR FQPYMQEVVP FLARLSNRLS TCHIEGDDLH IQRN-VQKLKD 151 TVKKLGESGE IKAIGELDLL FMSLR-NACI (SEQ ID NO:2)

Clone "IL-22" was deposited on Apr. 28, 1999 with the American Type Culture Collection (10801 University Boulevard, Manassas, Va. 20110-2209 U.S.A.) as an original deposit under the Budapest Treaty and were given the accession number ATCC 207231. All restrictions on the availability to the public of the deposited material will be irrevocably removed upon the granting of the patent, except for the requirements specified in 37 C.F.R. §1.808(b), and the term of the deposit will comply with 37 C.F.R. §1.806.

Nucleotide sequences encoding murine IL-22, and the sequence of the encoded polypeptide, are provided below:

```
   1   GAATTCGGCC AAAGAGGCCT ACCTAAACAG GCTCTCCTCT CAGTTATCAA
  51   CTGTTGACAC TTGTGCGATC TCTGATGGCT GTCCTGCAGA AATCTATGAG
 101   TTTTTCCCTT ATGGGGACTT TGGCCGCCAG CTGCCTGCTT CTCATTGCCC
 151   TGTGGGCCCA GGAGGCAAAT GCGCTGCCCG TCAACACCCG GTGCAAGCTT
 201   GAGGTGTCCA ACTTCCAGCA GCCATACATC GTCAACCGCA CCTTTATGCT
 251   GGCCAAGGAG GCCAGCCTTG CAGATAACAA CACAGATGTC CGGCTCATCG
 301   GGGAGAAACT GTTCCGAGGA GTCAGTGCTA AGGATCAGTG CTACCTGATG
 351   AAGCAGGTGC TCAACTTCAC CCTGGAAGAC GTTCTGCTCC CCCAGTCAGA
 401   CAGGTTCCAG CCCTACATGC AGGAGGTGGT GCCrTTCCTG ACCAAACTCA
 451   GCAATCAGCT CAGCTCCTGT CACATCAGCG GTGACGACCA GAACATCCAG
 501   AAGAATGTCA GAAGGCTGAA GGAGACAGTG AAAAAGCTTG GAGAGAGTGG
 551   AGAGATCAAG GCGATTGGGG AACTGGACCT GCTGTTTATG TCTCTGAGAA
 601   ATGCTTGCGT CTGAGCGAGA AGAAGCTAGA AAACGAAGAA CTGCTCCTTC
 651   CTGCCTTCTA AAAAGAACAA TAAGATCCCT GAATGGACTT TTTTACTAAA
 701   GGAAAGTGAG AAGCTAACGT CCATCATTAT TAGAAGATTT CACATGAAAC
 751   CTGGCTCAGT TGAAAAAGAA AATAGTGTCA AGTTGTCCAT GAGACCAGAG
 801   GTAGACTTGA TAACCACAAA GATTCATTGA CAATATTTTA TTGTCACTGA
 851   TGATACAACA GAAAAATAAT GTACTTTAAA AAATTGTTTG AAAGGAGGTT
 901   ACCTCTCATT CCTTTAGAAA AAAAGCTTAT GTAACTTCAT TTCCATAACC
 951   AATATTTTAT ATATGTAAGT TTATTTATTA TAAGTATACA TTTTATTTAT
1001   GTCAGTTTAT TAATATGGAT TTATTTATAG AAACATTATC TGCTATTGAT
1051   ATTTAGTATA AGGCAAATAA TATTTATGAC AATAACTATG GAAACAAGAT
1101   ATCTTAGGCT TTAATAAACA CATGGATATC ATAAAAAAAA AAAAAAAAA
1151   AAAAAAAGC GGCCGC (SEQ ID NO: 3)
```

The amino acid sequence of the polypeptide encoded by the above-referenced polynucleotide sequence is provide below:

```
  1   MAVLQKSMSF SLMGTLAASC LLLIALWAQE ANALPVNTRC KLEVSNFQQP
 51   YIVNRTFMLA KEASLADNNT DVRLIGEKLF RGVSAKDQCY LMKQVLNFTL
101   EDVLLPQSDR FQPYMQEVVP FLTKLSNQLS SCHISGDDQN IQKNVRRLKE
151   TVKKLGESGE IKAIGELDLL FMSLRNACV* (SEQ ID NO: 4)
```

Fragments of an IL-22 protein (e.g. fragments which are capable of exhibiting biological activity) are also encompassed by the compositions and methods of the invention. Fragments of the protein can be in linear form, or they can be cyclized using known methods, for example, as described in H. U. Saragovi, et al., Bio/Technology 773-778 (1992) and in R. S. McDowell, et al., J. Amer. Chem. Soc. 114, 9245-9253 (1992), both of which are incorporated herein by reference. Such fragments can be fused to carrier molecules such as immunoglobulins for many purposes, including increasing the valency of protein binding sites. For example, fragments of the protein can be fused through "linker" sequences to the Fc portion of an immunoglobulin. For a bivalent form of the protein, such a fusion can be to the Fc portion of an IgG molecule. Other immunoglobulin isotypes may also be used to generate such fusions. For example, a protein-IgM fusion generates a decavalent form of the protein of the invention.

The present invention also provides both full-length and mature forms of the disclosed proteins. The full-length form of such proteins is identified in the sequence listing by translation of the nucleotide sequence of each disclosed clone. The mature form(s) of such protein can be obtained by expression of the disclosed full-length polynucleotide. (preferably those deposited with ATCC) in a suitable mammalian cell or other host cell. The sequence(s) of the mature form(s) of the protein can also be determined from the amino acid sequence of the full-length form. An example of a mature IL-22 polypeptide sequence is amino acids 1-179 of SEQ ID NO:2.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

The chromosomal location corresponding to the polynucleotide sequences disclosed herein may also be determined, for example by hybridizing appropriately labeled polynucleotides of the present invention to chromosomes in situ. The corresponding chromosomal location for a disclosed polynucleotide can be determined by identifying significantly similar nucleotide sequences in public databases, such as expressed sequence tags (ESTs), that have already been mapped to particular chromosomal locations. For at least some of the polynucleotide sequences disclosed herein, public database sequences having at least some similarity to the polynucleotide of the present invention have been listed by database accession number. Searches using the GenBank accession numbers of these public database sequences can then be performed at an Internet site provided by the National Center for Biotechnology Information having the address http://www.ncbi.nlm.nih.gov/UniGene/, in order to identify "UniGene clusters" of overlapping sequences. Many of the "UniGene clusters" so identified will already have been mapped to particular chromosomal sites.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, *Trends Pharmacol. Sci.* 15(7): 250-254; Lavarosky et al., 1997, *Biochem. Mol. Med.* 62(1): 11-22; and Hampel, 1998, *Prog. Nucleic Acid Res. Mol. Biol.* 58: 1-39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, *Bioessays* 14(9): 629-633; Zwaal et al., 1993, *Proc. Natl. Acad. Sci. USA* 90(16): 7431-7435; Clark et al., 1994, *Proc. Natl. Acad. Sci. USA* 91(2): 719-722; all of which are incorporated by reference herein), or through homologous recombination, preferably detected by positive/negative genetic selection strategies (Mansour et al., 1988, *Nature* 336: 348-352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms, part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information. For example, the TopPredII computer program can be used to predict the location of transmembrane domains in an amino acid sequence, domains which are described by the location of the center of the transmembrane domain, with at least ten transmembrane amino acids on each side of the reported central residue(s).

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

In another embodiment, proteins, protein fragments, and recombinant proteins of the present invention include those which can be identified based on the presence of at least one "IL-22 receptor-binding motif." As used herein, the term "IL-22 receptor-binding motif" includes amino acid sequences or residues which are important for binding of IL-22 to its requisite receptor. In a preferred embodiment, a IL-22 protein contains a IL-22 receptor-binding motif including about amino acids 50-60 of SEQ ID NO:2. In another embodiment, an IL-22 protein contains a IL-22 receptor-binding motif including about amino acids 63-81 of SEQ ID NO:2. In yet another embodiment, an IL-22 protein contains a IL-22 receptor-binding motif including about amino acids 168-177 of SEQ ID NO:2. In a preferred embodiment, an IL-22 protein contains a IL-22 receptor-binding motif including at least one of amino acids 50-60, amino acids 63-81, and/or about amino acids 168-177 of SEQ ID NO:2.

In yet another embodiment, a IL-22 receptor binding motif has an amino acid sequence at least 95%, 96%, 97%, 98%, 99%, or more identical to an amino acid sequence selected from the group consisting of amino acids 50-60 of SEQ ID NO:2, amino acids 63-81 of SEQ ID NO:2, and amino acids 168-177 of SEQ ID NO:2.

In another embodiment, proteins, protein fragments, and recombinant proteins of the present invention include those which can be identified based on the presence of at least one, two, three, four or more sites for N-linked glycosylation.

In particular, sequence identity can be determined using WU-BLAST (Washington University BLAST) version 2.0 software, which builds upon WU-BLAST version 1.4, which in turn is based on the public domain NCBI-BLAST version 1.4 (Altschul and Gish, 1996, Local alignment statistics, Doolittle ed., *Methods in Enzymology* 266: 460-480; Altschul et al., 1990, Basic local alignment search tool, *Journal of Molecular Biology* 215: 403-410; Gish and States, 1993, Identification of protein coding regions by database similarity search, *Nature Genetics* 3: 266-272; Karlin and Altschul, 1993, Applications and statistics for multiple high-scoring segments in molecular sequences, *Proc. Natl. Acad. Sci. USA* 90: 5873-5877; all of which are incorporated by reference herein). WU-BLAST version 2.0 executable programs for several UNIX platforms can be downloaded from ftp://blast.wustl.edu/blast/executables. The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite—BLASTP, BLASTN, BLASTX, TBLASTN and TBLASTX—the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but can be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but can be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Species homologues of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75%, 80%, 85%, 90%, 95%, 99%) with the given polynucleotide, and protein species homologues have at least 30% sequence identity (more preferably, at least 45%, 50%, 55%, 60%, 65%, 70%, 75%, 80%, 85%, 90%) with the given protein, where sequence identity is determined by comparing the nucleotide sequences of the polynucleotides or the amino acid sequences of the proteins when aligned so as to maximize overlap and identity while minimizing sequence gaps. Species homologues can be isolated and identified by making suitable probes or primers from the sequences provided herein and screening a suitable nucleic acid source from the desired species. Preferably, species homologues are those isolated from mammalian species. Most preferably, species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Mus musculus, Rattus norvegicus, Cricetulus griseus, Felis catus, Mustela vison, Canis familiaris, Oryctolagus cuniculus, Bos taurus, Ovis aries, Sus scrofa*, and *Equus caballus*, for which genetic maps have been created allowing the identification of syntenic relationships between the genomic organization of genes in one species and the genomic organization of the related genes in another species (O'Brien and Seuánez, 1988, *Ann. Rev. Genet.* 22: 323-351; O'Brien et al., 1993, *Nature Genetics* 3:103-112; Johansson et al., 1995, *Genomics* 25: 682-690; Lyons et al., 1997, *Nature Genetics* 15: 47-56; O'Brien et al., 1997, *Trends in Genetics* 13(10): 393-399; Carver and Stubbs, 1997, *Genome Research* 7:1123-1137; all of which are incorporated by reference herein)

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75%, 80%, 85%, 90%, 95%, 99%) with the given polynucleotide, where sequence identity is determined by comparing the nucleotide sequences of the polynucleotides when aligned so as to maximize overlap and identity while minimizing sequence gaps. Allelic variants can be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

The present invention also includes polynucleotides that hybridize under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A-F; stringent conditions are at least as stringent as, for example, conditions G-L; and reduced stringency conditions are at least as stringent as, for example, conditions M-R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | ≥50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | ≥50 | 70° C.; 1 × SSC -or- 50° C.; 1 × SSC, 50% formamide | 70° C.; 0.3 × SSC |
| F | RNA:RNA | <50 | $T_F$*; 1 × SSC | $T_F$*; 1 × SSC |
| G | DNA:DNA | ≥50 | 65° C.; 4 × SSC -or- 42° C.; 4 × SSC, 50% formamide | 65° C.; 1 × SSC |
| H | DNA:DNA | <50 | $T_H$*; 4 × SSC | $T_H$*; 4 × SSC |
| I | DNA:RNA | ≥50 | 67° C.; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | ≥50 | 70° C.; 4 × SSC -or- 50° C.; 4 × SSC, 50% formamide | 67° C.; 1 × SSC |
| L | RNA:RNA | <50 | $T_L$*; 2 × SSC | $T_L$*; 2 × SSC |
| M | DNA:DNA | ≥50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | ≥50 | 55° C.; 4 × SSC -or- 42° C.; 6 × SSC, 50% formamide | 55° C.; 2 × SSC |
| P | DNA:RNA | <50 | $T_P$*; 6 × SSC | $T_P$*; 6 × SSC |
| Q | RNA:RNA | ≥50 | 60° C.; 4 × SSC -or- 45° C.; 6 × SSC, 50% formamide | 60° C.; 2 × SSC |
| R | RNA:RNA | <50 | $T_R$*; 4 × SSC | $T_R$*; 4 × SSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE (1 × SSPE is 0.15M NaCl, 10 mM $NaH_2PO_4$, and 1.25 mM EDTA, pH 7.4) can be substituted for SSC (1 × SSC is 0.15M NaCl and 15 mM sodium citrate) in the hybridization and wash buffers; washes are performed for 15 minutes after hybridization is complete.
*$T_B$ – $T_R$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(%G + C) – (600/N), where N is the number of bases in the hybrid, and [$Na^+$] is the concentration of sodium ions in the hybridization buffer ([$Na^+$] for 1 × SSC = 0.165M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor. Laboratory Press, Cold Spring Harbor, N.Y., chapters 9 and 11, and *Current Protocols in Molecular Biology,* 1995; F. M. Ausubel et al., eds., John Wiley & Sons, Inc., sections 2.10 and 6.3-6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

II. Vectors and Host Cells

The isolated polynucleotide of the invention can be operably linked to an expression control sequence such as the pMT2 or pED expression vectors disclosed in Kaufman et al., Nucleic Acids Res. 19, 4485-4490 (1991), in order to produce the protein recombinantly. Many suitable expression control sequences are known in the art. General methods of expressing recombinant proteins are also known and are exemplified in R. Kaufman, Methods in Enzymology 185, 537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/ expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it can be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida,* or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it can be necessary to modify the protein produced therein, for example by phosphorylation or glycosylation of the appropriate sites, in order to obtain the functional protein. Such covalent attachments can be accomplished using known chemical or enzymatic methods. The protein may also be modified by covalent modifications including, but not limited, polyethylene glycol modifications.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. As used herein, an insect cell capable of expressing a polynucleotide of the present invention is "transformed."

The protein of the invention can be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it can be expressed as a fusion protein, such as those of maltose binding protein (MBP), glutathione-S-transferase (GST) or thioredoxin (TRX). Kits for expression and purification of such fusion proteins are commercially available from New England BioLabs (Beverly, Mass.), Pharmacia (Piscataway, N.J.) and Invitrogen Corporation (Carlsbad, Calif.), respectively. The protein can also be tagged with an epitope and subsequently purified by using a specific antibody directed to such epitope. One such epitope ("Flag") is commercially available from the Eastman Kodak Company (New Haven, Conn.).

In addition, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they can be employed as biologically active or immunological substitutes for natural, purified proteins in screening of therapeutic compounds and in immunological processes for the development of antibodies.

The protein may also be produced in a recombinant viral vector through techniques that are well-known in the art. For example, recombinant adenoviruses, such as the Ad5 E1a deleted (dl327) recombinant adenovirus, can be generated through homologous recombination in a human kidney embryonic cell line. IL-22 cDNA can then be ligated into an adenovirus vector such as Adori 1-2. The cloned viral vector can then be administered to a subject via subcutaneous or intravenous injection to allow for in vivo production of the invention.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues can be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

III. Methods of Use and Biological Activity

The polynucleotides and proteins of the present invention can exhibit one or more of the biological activities (including those associated with assays cited herein) identified below and accordingly are useful in a variety of research, pharmaceutical and therapeutic methods. Methods, uses or activities described for proteins of the present invention can be provided by administration or use of such proteins or by administration or use of polynucleotides encoding such proteins (such as, for example, in gene therapies or vectors suitable for introduction of DNA).

The structural and functional properties of IL-22 place this protein in the cytokine family. Cytokines play important roles both in health and disease and have multiple clinical indications. As is described in detail in the Examples, below, IL-22 induces changes associated with those caused by inflammatory cytokines (such as IL-1 and TNFα), and inhibitors of IL-22 ameliorate symptoms of rheumatoid arthritis, Therefore, IL-22, and/or agents that increase levels of IL-22 or mimic the actions of IL-22 (and other molecules of the present invention) are useful as agonists in certain clinical indications, and antagonists of this molecule are useful in other clinical situations, particularly in those in which modulation of an inflammatory state is desired. Whether the agonist or antagonist is the preferred depends on the particular aspects of the disease pathology, such as the cell types involved, the nature of the stimulus and the cellular microenvironment.

In a preferred embodiment, IL-22 activity includes induction of at least one activity indicative of an inflammatory state. Additional activities can include at least one or more of the following activities: (1) modulating, for example antagonizing a signal transduction pathway (e.g. an IL-22 dependant pathway); (2) modulating cytokine production and/or secretion (e.g. production and/or secretion of a proinflammatory cytokine); (3) modulating lymphokine production and/or secretion; (4) modulating production of adhesion molecules and/or cellular adhesion; (5) modulating expression or activity of nuclear transcription factors; (7) modulating secretion of IL-1; (8) competing with receptors for other cytokines; (9) competing with another IL-22 family member protein to bind a IL-22 receptor; (10) modulating nuclear translocation of internalized receptor for IL-22 or another cytokine or ligand-complexed receptor, (11) modulating cell proliferation, development or differentiation, for example, cytokine-stimulated or a IL-22 protein-stimulated proliferation, development or differentiation (e.g., of an epithelial cell, for example, a squamous epithelial cell of the esophagus, or of a skin cell, e.g., a keratinocyte); (12) modulating cell proliferation, development or differentiation of an osteogenic cell (e.g., of an osteoclast precursor cell, osteoclast and/or osteoblast); (13) modulating bone formation, bone metabolism and/or bone homeostasis (e.g., inhibiting bone resorption); (15) modulating cellular immune responses; (16) modulating cytokine-mediated proinflammatory actions (e.g., inhibiting acute phase protein synthesis by hepatocytes, fever, and/or prostaglandin synthesis, for example $PGE_2$ synthesis); and (17) promoting and/or potentiating wound healing.

Examples of IL-22 inhibitors include soluble fragments of IL-22 polypeptides. The soluble fragments can be provided as fusion proteins, e.g., as IgG fusion proteins. Inhibitors can additionally include antibodies to IL-22 polypeptides, as well as small molecule inhibitors of IL-22 polypeptides. The small molecules can act by inhibiting the expression and/or activity of an IL-22 polypeptide.

A: Diagnostic Assays

An exemplary method for detecting the presence or absence of IL-22 protein or nucleic acid in a biological sample involves obtaining a biological sample from a test subject and contacting the biological sample with a compound or an agent capable of detecting IL-22 protein or nucleic acid (e.g., mRNA, genomic DNA) that encodes IL-22 protein such that the presence of IL-22 protein or nucleic acid is detected in the biological sample. A preferred agent for detecting IL-22 mRNA or genomic DNA is a labeled nucleic acid probe capable of hybridizing to IL-22 mRNA or genomic DNA. The nucleic acid probe can be, for example, a full-length IL-22 nucleic acid, such as the nucleic acid of SEQ ID NO: 1, or a fragment or portion of an IL-22 nucleic acid such as an oligonucleotide of at least 15, 30, 50, 100, 250 or 500 nucleotides in length and sufficient to specifically hybridize under stringent conditions to IL-22 mRNA or genomic DNA. Other suitable probes for use in the diagnostic assays of the invention are described herein.

A preferred agent for detecting IL-22 protein is an antibody capable of binding to IL-22 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect IL-22 mRNA, protein, or genomic DNA in a biological sample in vitro as well as in vivo. For example, in vitro techniques for detection of IL-22 mRNA include Northern hybridizations and in situ hybridizations. In vitro techniques for detection of IL-22 protein include enzyme linked immunosorbent assays (ELISAs), Western blots, immunoprecipitations and immunofluorescence. In vitro techniques for detection of IL-22 genomic DNA include Southern hybridizations. Furthermore, in vivo techniques for detection of IL-22 protein include introducing into a subject a labeled anti-IL-22 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting IL-22 protein, mRNA, or genomic DNA, such that the presence of IL-22 protein, mRNA or genomic DNA is detected in the biological sample, and comparing the presence of IL-22 protein, mRNA or genomic DNA in the control sample with the presence of IL-22 protein, mRNA or genomic DNA in the test sample.

The invention also encompasses kits for detecting the presence of IL-22 in a biological sample. For example, the kit can comprise a labeled compound or agent (e.g. probe or antibody) capable of detecting IL-22 protein or mRNA in a biological sample; means for determining the amount of IL-22 in the sample; and means for comparing the amount of IL-22 in the sample with a standard. The compound or agent can be packaged in a suitable container. The kit can further comprise instructions for using the kit to detect IL-22 protein or nucleic acid.

Human. IL-22 agonists include without limitation human IL-22 proteins and fragments, deletion mutants and addition mutants thereof; and peptide and small molecule compounds that interact with the receptor or other target, to which human IL-22 is directed. Human IL-22 antagonists include without limitation antibodies directed to human IL-22 proteins; soluble forms of the receptor or other target to which human IL-22 is directed; antibodies directed to the receptor or other target to which human IL-22 is directed; and peptide and small molecule compounds that inhibit or interfere with the interaction of human IL-22 with its receptor or other target.

B. Pharmaceutical Compositions

The nucleic acid molecules, proteins, modulatory agents; and/or antibodies and biosynthetic molecules (also referred to herein as "active compounds") of the invention can be incorporated into pharmaceutical compositions suitable for administration. Such compositions typically comprise the nucleic acid molecule, protein, modulatory agents, and/or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. The pharmaceutical composition of the invention may also contain additional cytokines, lymphokines, or other hematopoietic factors. The pharmaceutical composition may further contain other agents which either enhance the activity of the protein or compliment its activity or use in treatment.

Thus, the pharmaceutical composition of the invention may also contain additional cytokines, lymphokines, or other hematopoietic factors such as M-CSF, G-CSF, GM-CSF, Meg-GCSF, thrombopoietin, stem cell factor, erythropoietin, TNFα, IL-1β, IL-2 through IL-26, IFNα/b, IFNγ, as well as inhibitors of all of the above cytokines, particularly inhibitors of TNFα, IL-10, IL-12 and IL-18.

Such additional factors and/or agents can be included in the pharmaceutical composition to produce a synergistic effect with protein of the invention, or to minimize side effects. Conversely, protein of the present invention can be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention can be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention can be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention can be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Immunomodulin protein or anti-Immunomodulin antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, a "therapeutically effective" dose can be estimated initially from cell culture assays. A "therapeutically effective" dose can be further formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. ex vivo The pharmaceutical compositions can be included in a container, pack, or dispenser together with instructions for administration.

C. Therapeutic Uses

The present invention provides for both prophylactic and therapeutic methods of treating subjects (e.g., human subjects). In one aspect, the invention provides a method for preventing or treating a disease or a disorder in a subject prophylactically or therapeutically. Administration of an agent prophylactically can occur prior to the manifestation of symptoms of an undesired disease or disorder, such that the disease or disorder is prevented or, alternatively, delayed in its progression. The prophylactic methods of the present invention can be carried out in a similar manner to therapeutic methods described herein, although dosage and treatment regimes may differ.

Another aspect of the invention pertains to methods for treating a subject therapeutically. In one embodiment, the present invention includes methods of modulating an immune response. In particular, modulation of an immune response includes, but is not limited to, modulation of cellular toxicity, modulation of cytokine expression, production or secretion (e.g., enhancement or inhibition of cytokine expression, production or secretion). A preferred embodiment of the invention involves modulation of IL-22, in particular, stimulation of IL-22 using a IL-22 stimulatory modulator or, alternatively, inhibition of IL-22 using a IL-22 inhibitory modulator. Accordingly, the present method has therapeutic utility in biasing an immune response towards, or away from, a natural immunity-type response depending upon the desired therapeutic regimen. Such modulatory methods are particularly useful in diseases such as viral and bacterial infection, in particular acute phase responses, sepsis and autoimmune disorders (i.e. chronic inflammatory states). Moreover, the immunomodulatory methods of the present invention can be used to treat an immunocompromised individual to enhance immunity. Uses to increase resistance to viral infection and enhance the rejection of foreign molecules are also within the scope of the present invention. The immunomodulatory methods of the present invention are further useful in treating sepsis. For example, an inhibition of cytokines such as IL-22 and Tumor Necrosis Factor in patients infected with gram negative bacteria can result in an attenuated immune response, thus preventing septic shock. The immunomodulatory methods of the present invention are further useful in treating acute phase responses and chronic inflammatory diseases.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "treatment" includes the application or administration of a therapeutic agent to a subject or to an isolated tissue or cell line from a subject, who is afflicted with a disease, a symptom of disease or a predisposition toward a disease, with the goal of curing, healing, alleviating, relieving, altering, remedying, ameliorating, improving or affecting the disease, the symptoms of disease or the predisposition toward disease.

In practicing the method of treatment or use of the present invention, a therapeutically effective amount of protein of the present invention is administered to a mammal having a condition to be treated. Protein of the present invention can be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention can be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such, as water, petroleum, oils of animal or plant origin such as peanut oil, mineral oil, soybean oil, or sesame oil, or synthetic oils can be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention can be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 ng to about 10 mg, more preferably about 0.1 µg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

In a preferred embodiment, pharmaceutical preparations (e.g. those comprising neutralizing agents against) of the present invention will be administered 2 to 6 hours after onset of infection. For example, in vitro assays suggest that adherent compartment of peritoneal exudate cells produce IL-22 2 to 6 hours after treatment with LPS, suggesting that IL-22 is produced early in an immune response. Accordingly, early administration of, for example, neutralizing agents, during the course of infection may enhance the therapeutic efficacy of such agents.

Protein of the invention may also be used to immunize animals to obtain polyclonal and monoclonal antibodies which specifically react with the protein. As used herein, the term "antibody" includes without limitation a polyclonal antibody, a monoclonal antibody, a chimeric antibody, a single-chain antibody, a CDR-grafted antibody, a humanized antibody, or fragments thereof which bind to the indicated protein. Such term also includes any other species derived from an antibody or antibody sequence which is capable of binding the indicated protein.

Antibodies to a particular protein can be produced by methods well known to those skilled in the art. For example, monoclonal antibodies can be produced by generation of antibody-producing hybridomas in accordance with known methods (see for example, Goding, 1983, Monoclonal antibodies: principles and practice, Academic Press Inc., New York; and Yokoyama, 1992, "Production of Monoclonal Antibodies" in Current Protocols in Immunology, Unit 2.5, Greene Publishing Assoc. and John Wiley & Sons). Polyclonal sera and antibodies can be produced by inoculation of a mammalian subject with the relevant protein or fragments thereof in accordance with known methods. Examples of suitable methods include direct DNA gene or viral (e.g., adenovirus or retroviral) administration to an animal. Fragments of antibodies, receptors, or other reactive peptides can be produced from the corresponding antibodies by cleavage of and collection of the desired fragments in accordance with known methods (see for example, Goding, supra; and Andrew et al., 1992, "Fragmentation of Immunoglobulins" in Current Protocols in Immunology, Unit 2.8, Greene Publishing Assoc. and John Wiley & Sons). Chimeric antibodies and single chain antibodies can also be produced in accordance with known recombinant methods (see for example, U.S. Pat. No. 5,169,939, U.S. Pat. No. 5,194,594, and U.S. Pat. No. 5,576,184). Humanized antibodies can also be made from corresponding murine antibodies in accordance with well known methods (see for example, U.S. Pat. Nos. 5,530,101, 5,585,089, and 5,693,762). Additionally, human antibodies can be produced in non-human animals such as mice that have been genetically altered to express human antibody molecules (see for example Fishwild et al., 1996, *Nature Biotechnology* 14: 845-851; Mendez et al., 1997, *Nature Genetics* 15: 146-156 (erratum *Nature Genetics* 16: 410); and U.S. Pat. Nos. 5,877,397 and 5,625,126). Such antibodies can be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149-2154 (1963); J. L. Krstenansky, et al., FEBS Lett. 211, 10 (1987).

Monoclonal antibodies binding to the protein of the invention is useful as diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein are useful in detecting and preventing the metastatic spread of the cancerous cells, which can be mediated by the protein.

In a preferred embodiment, monoclonal and polyclonal antibodies are used to down-modulate an immune response. Examples of immunological conditions which can benefit from such treatment include bacterial infections (i.e. induction of sepsis that can lead to septic shock and/or septicemia) and other chronic inflammatory conditions such as rheumatoid arthritis and osteoarthritis.

Agents which modulate the activity of the present invention are also used to alter the inflammatory pathologies of the kidney.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration can be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices can be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions can be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are non-biodegradable and chemically defined, such as sintered hydroxapatite, bioglass, aluminates, or other ceramics. Matrices can be comprised of combinations of any of the above mentioned types of material, such as polylactic acid and hydroxyapatite or collagen and tricalciumphosphate. The bioceramics can be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention can be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

D. Screening Assays

The proteins provided by the present invention can be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowman et al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028-3033, 1990; and Assays for B cell function: In vitro antibody production, Mond, J. J. and Brunswick, M. In *Current Protocols in Immunology*. J. E. e. a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500, 1986; Takai et al., J. Immunol. 140:508-512, 1988; Bertagnolli et al., J. Immunol. 149:3778-3783, 1992.

Dendritic cell-dependent assays (which will identify, among others, proteins expressed by dendritic cells that activate naive T-cells) include, without limitation, those described in: Guery et al, J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264, 1989; Bhardwaj et al., Journal of Clinical Investigation 94:797-807, 1994; and Inaba et al., Journal of Experimental Medicine 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, Journal of Immunology 145:4037-4045, 1990; Zamai et al., Cytometry 14:891-897, 1993; Gorczyca et al., International Journal of Oncology 1:639-648, 1992.

Assays for proteins that influence early steps of T-cell commitment and development include, without limitation, those described in: Antica et al., Blood 84:111-117, 1994; Fine et al., Cellular Immunology 155:111-122, 1994; Galy et al., Blood 85:2770-2778, 1995; Toki et al., Proc. Nat. Acad Sci. USA 88:7548-7551, 1991.

Modulatory agents identified by the above-described screening assays are tested in an appropriate animal model, for example, to determine the efficacy, toxicity, or side effects of treatment with such an agent. Alternatively, modulatory agents are tested in at least one of the in vitro or in situ assays described herein.

In another aspect of the invention, transgenic and gene knockout animals are used to study disease. Specifically, mice that have been genetically altered to express a disease phenotype are used to screen agents that modulate IL-22 activity. As used herein, the term "genetically altered" means any animal that has manipulated genetically, either by the introduction of a heterologous gene encoding a protein (a transgenic animal) or by the deletion of a gene by homologous recombination (a gene knockout animal). Preferably, the animal that has been genetically altered is a mouse.

In another embodiment, IL-22 molecules (e.g. RNA, DNA, cDNA, protein or antibodies) are used as diagnostic tools, e.g., to detect the presence of tissues in an inflammatory state.

Assaying Effects of IL-22 Modulators

The activity of an IL-22 agonist or antagonist can be measure by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Bertagnolli et al., J. Immunol. 145:1706-1712, 1990; Bertagnolli et al., Cellular Immunology 133: 327-341, 1991; Bertagnolli, et al., J. Immunol. 149:3778-3783, 1992; Bowman et al., J. Immunol. 152: 1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E. Coligan eds. Vol 1 pp. 3.12.1-3.12.14, John Wiley and Sons, Toronto. 1994; and Measurement of mouse and human Interferon γ, Schreiber, R. D. In *Current Protocols in Immunology*. J. E. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e. a. Coligan eds. Vol 1 pp. 6.3.1-6.3.12, John Wiley and Sons, Toronto. 1991; de Vries et al., J. Exp. Med. 173:1205-1211, 1991; Moreau et al., Nature 336:690-692, 1988; Greenberger et al., Proc. Natl. Acad. Sci. U.S.A. 80:2931-2938, 1983; Measurement of mouse and human interleukin 6—Nordan, R. In *Current Protocols in Immunology*. J. E. e. a. Coligan eds. Vol 1 pp. 6.6.1-6.6.5, John Wiley and Sons, Toronto. 1991; Smith et al., Proc. Natl. Acad. Sci. U.S.A. 83:1857-1861, 1986; Measurement of human Interleukin 11—Bennett, F., Giannotti, J., Clark, S. C. and Turner, K. J. In *Current Protocols in Immunology*. J. E. e. a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology*. J. E. e. a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

Immune Stimulating or Suppressing Activity

An IL-22 modulator may also exhibit immune stimulating or immune suppressing activity, including without limitation the activities for which assays are described herein. An IL-22 agonist is useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies can be genetic or be caused by viral (e.g., HIV) as well as bacterial or fungal infections, or may result from autoimmune disorders. More specifically, infectious diseases causes by viral, bacterial, fungal or other infection can be treatable using a protein of the present invention, including infections by HIV, hepatitis viruses, herpesviruses, mycobacteria, *Leishmania* spp., *malaria* spp. and various fungal infections such as candidiasis. An IL-22 protein is also useful where a boost to the immune system generally can be desirable, i.e., in the treatment of cancer.

An IL-22 inhibitor (such as an IL-22 antibody) can be used to treat an autoimmune disorder. Autoimmune disorders that can be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention can also be used to treat inflammatory conditions associated with, e.g., pancreatitis. IL-22 inhibitors are also useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses in a number of ways. Down regulation can be in the form of inhibiting or blocking an immune response already in progress or may involve preventing the induction of an immune response. The functions of activated T cells, can be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

As used herein, the term "pathological condition" refers to the structural and functional consequences of injurious stimuli on cells, tissues, and organs and ultimately the consequences on the entire organism. Such injurious stimuli includes, but is not limited to, infection with a foreign body (i.e. bacteria, virus, fungi and parasite), inflammation, autoimmune disorders (i.e. rheumatoid arthritis, osteoarthritis, multiple sclerosis, myasthenia gravis, inflammatory bowel diseases, diabetes, SLE, and psoriasis), cancer, necrosis, ischemia, acute phase responses, apoptosis, wound healing processes, cholesterol metabolism, oxygen free radical injury, atherosclerosis and allergies.

In a particular embodiment, the down-regulation or preventing of one or more activities of the IL-22 molecules of present invention can be helpful in the treatment of sepsis. Briefly, sepsis is an out of control inflammatory response, often in response to various pus-forming and other pathogenic organisms (i.e. gram negative bacteria), or their toxins, in the blood or tissues. Agents that block the activity of IL-22 molecules of the present invention can, accordingly, attenuate the induction of septic shock.

In another embodiment, down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte, antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to energize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci. USA, 89:11102-11105 (1992). In addition, murine models of GVHD (see Paul ed., Fundamental Immunology, Raven Press, New York, 1989, pp. 846-847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor ligand interactions of B lymphocyte antigens can be used to inhibit T cell activation and prevent production of autoantibodies or T cell-derived cytokines which can be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856).

In a particular embodiment, IL-22 inhibitory agents (e.g. blocking agents) of the present invention can be used to treat autoimmune disease, in particular, lymphocyte-mediated autoimmune diseases, associated with prolonged acute phase responses that persist in the setting of chronic inflammation, such as rheumatoid arthritis, osteoarthritis, multiple sclerosis, inflammatory bowel disease, diabetes and Systemic Lupus Erythomatosis (SLE), atherosclerosis and allergies. In such a situation, persistent elevations of serum amyloid A protein may lead to deposition of this protein in the interstitium of tissues, a condition known as amyloidosis. The deposition of serum amyloid A in tissues is often in the form of fibrils rich in β-pleated sheet structures which can interfere with normal tissue function (i.e. myocardial contraction, glomerular filtration). Thus, inhibiting or blocking IL-22 production, for example, by a neutralizing antibody can help stop the acute phase reaction, and therefore prevent the occurrence of amyloidosis.

Upregulation of an antigen function (preferably a B lymphocyte antigen function), as a means of up regulating immune responses, may also be useful in therapy. Upregulation of immune responses can be in the form of enhancing an existing immune response or eliciting an initial immune response. For example, enhancing an immune response through stimulating B lymphocyte antigen function is useful in cases of viral infection. In addition, systemic viral diseases such as influenza, the common cold, and encephalitis might be alleviated by the administration of stimulatory forms of B lymphocyte antigens systemically.

Alternatively, anti-viral immune responses can be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In a particular embodiment, the IL-22 molecules and/or modulators of the present invention can be used as a vaccine adjuvant due to their ability to modulate the immune system. For example, the IL-22 molecules and/or modulators (e.g. positive modulatory agents) of the present invention can be co-administered with a potential vaccine antigen in order to elicit a nonspecific inflammatory immune response to the potential vaccine antigen. Such vaccines can be directed against a foreign organism (i.e. bacteria, virus, parasite or fungi) or a tumor antigen. Moreover, such treatments may include, but are not limited to, gene transfer with IL-22 DNA.

As used herein, the term "immunogenicity-augmenting" includes enhancing and/or increasing the immunogenicity of, for example, a vaccine, as compared to such vaccine in the absence of IL-22.

In another application, up regulation or enhancement of antigen function (preferably B lymphocyte antigen function) is useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I a chain protein and $\beta_2$ microglobulin protein or an MHC class II a chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject can be sufficient to overcome tumor-specific tolerance in the subject.

Hematopoiesis Regulating Activity

An IL-22 protein, or modulator can also be used to regulate hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141-151, 1995; Keller et al., Molecular and Cellular Biology 13:473-486, 1993; McClanahan et al., Blood 81:2903-2915, 1993.

Assays for stem cell survival and differentiation (which will identify, among others, proteins that regulate lympho-hematopoiesis) include, without limitation, those described in: Methylcellulose colony forming assays, Freshney, M. G. In *Culture of Hematopoietic Cells*. R. I. Freshney, et al. eds. Vol pp. 265-268, Wiley-Liss, Inc., New York, N.Y. 1994; Hirayama et al., Proc. Natl. Acad. Sci. USA 89:5907-5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23-39, Wiley-Liss, Inc., New York, N.Y. 1994; Neben et al., Experimental Hematology 22:353-359, 1994; Cobblestone area forming cell assay, Ploemacher, R. E. In *Culture of Hematopoietic Cells*. R. I. Freshney, et al. eds. Vol pp. 1-21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163-179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139-162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that can be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendonitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein can be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which can be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

A protein of the present invention also exhibits activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects can be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

In a preferred embodiment, the present invention is used for the re-modeling of kidney tissue, both ex vivo and in vivo. For example, exogenous IL-22 induces the generation of epithelial tissue in the proximal tubules of the kidney.

A protein of the present invention is also useful for promoting or inhibiting differentiation of tissues described above from precursor tissues or cells; or for inhibiting the growth of tissues described above.

The activity of a protein of the invention can be measured by methods known in the art. Some of these are described below:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pps. 71-112 (Maibach, H I and Rovee, D T, eds.), Year Book Medical Publishers, Inc., Chicago, as modified by Eaglstein and Mertz, J. Invest. Dermatol 71:382-84 (1978).

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131-140, 1986; Burdick et al., Thrombosis Res. 45:413-419, 1987; Humphrey et al., Fibrinolysis 5:71-79 (1991); Schaub, Prostaglandins 35:467-474, 1988.

Anti-Inflammatory Activity

IL-22 antagonists can be used as anti-inflammatory agents. Suitable conditions (including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Additional indications include anaphylaxis and hypersensitivity to an antigenic substance or material.

This invention is further illustrated by the non-limiting examples. The contents of all references, patents and pub-

EXAMPLES

Example 1

Identification and Characterization of Clone "IL-22"

A polynucleotide of the present invention has been identified as clone "IL-22". Clone IL-22 was isolated according to the following method. A murine EST was identified from a murine cDNA library made from splenocytes activated with both ConA and bone marrow derived dendritic cells. The EST was identified using methods which are selective for cDNAs encoding secreted proteins (see U.S. Pat. No. 5,536,637). The murine EST sequence was used to isolate a full-length murine clone from the same cDNA library. Analysis of the sequence of the murine clone revealed a significant homology to interleukin-10 (IL-10).

In order to isolate a human homolog of the murine clone, PCR primers were constructed based upon the region of the murine sequence which showed homology to IL-10. Use of such primers for amplification in a cDNA library derived from PHA/PMA-stimulated human PBMCs produced a PCR product of significant size. Analysis of the sequence of the PCR product confirmed that it was a homolog of the murine cDNA. Oligonucleotides were constructed from the sequence of the partial human clone and used to isolate a full-length human clone from the PBMC library.

IL-22 is a full-length human clone, including the entire coding sequence of a secreted protein (also referred to herein as "IL-22" protein). Analysis of its amino acid sequence indicated that it has about 23% homology to hIL-10. Based on the putative receptor-binding motifs in IL-10, three motifs involved with analogous function have been proposed in IL-22 through computer modeling. These are the regions of SEQ ID NO:2 from residue 50 to 60, from residue 63 to 81, and from residue: 168 to 177. Analyses of databases revealed that IL-22 also exhibits similar levels of homology with IL-10 of other species.

The nucleotide sequence of IL-22 as presently determined is reported in SEQ ID NO:1, and includes a poly(A) tail. The amino acid sequence of the IL-22 protein corresponding to the foregoing nucleotide sequence is reported in SEQ ID NO:2.

Example 2

Characterization of IL-22 Protein

Cell lines which stably express and secrete full length IL-22 protein were created by transfecting CHO cells with IL-22 cDNA in appropriate expression vectors. Transiently transfected COS cells using appropriate IL-22 expression vectors have been used to make IL-22 protein for analysis. Transfections were accomplished using the commercially available Lipofectamine reagent (Gibco). Interestingly, COS cells which express IL-22 were observed to non-uniformly detach, forming holes in the cell culture monolayer. Media conditioned by transfected COS cells was used to demonstrate cytokine-like activity of IL-22 protein. Western blot analysis of cell lysates showed that Stat-3 becomes phosphorylated (activated) in a kidney mesangial tissue-derived cell line exhibiting macrophage-like qualities (MES-13; see, Dumoutier et al (2000) *J. of Immunology* 164:1814-1819) upon exposure of that cell to media conditioned by IL-22-expressing cells. In addition phosphorylation of Stat-3 is induced in non-transfected COS cells that are treated with IL-22 protein.

Electrophoretic analysis of IL-22 protein (derived from the transfected COS cell lines described herein) indicated that the expressed protein exists in a range of sizes. Treatment of COS-derived IL-22 protein with N-glycanase prior to electrophoresis results in a single band corresponding to the highest mobility (e.g. lowest molecular weight) species seen in untreated IL-22. This is consistent with proposed glycosylation events which may occur at the putative N-linked glycosylation sites identified in the amino acid sequence of IL-22 (amino acid residues 54-56, 68-70, 97-99, and 176-178 of SEQ ID NO:2).

Edman N-terminal sequencing determined that the N-terminus of the mature IL-22 protein begins with the residue at position 34 of SEQ ID NO:2 (alanine). Expression vectors were created which fuse a "6× histidine" affinity tag and a FLAG epitope tag to the N-terminus of the mature IL-22 protein. (The added amino acid tag is given in SEQ ID NO:5 and has the following amino acid sequence: MKFLVN-VALVFMVVYISYIYAGSGHHHHHHGS-GDYKDDDDKAPISSHCR). These tagged constructs were used to create stably expressing CHO cell lines and transiently expressing COS cell lines. The tags provided a convenient means for detecting IL-22 (e.g., anti-6×his antibodies; anti-FLAG antibodies), and for purifying the protein from conditioned media (using $Ni^{+2}$ resin). Human IL-22 protein purified by this tag from the IL-22-expressing COS cell lines could used to induce Stat-3 activation in MES-13 cells.

Comparison of IL-22 mRNA transcripts in activated Th1 and Th2 cells (see, for example, Syrbe et al, (1999) *Springer Seminars in Immunopathology*, 21:263-85) indicated a substantially higher level of expression of IL-22 in activated Th1 cells than in activated Th2 cells. Analysis of IL-22 mRNA was accomplished with RNAse protection assays. Therefore, IL-22 is induced during an adaptive immune response, specifically by Th1 CD4+ T cells.

Example 3

Establishment of IL-22 Recombinant Adenovirus Vector and In Vivo Administration

The Adori 1-2 murine IL-22 (mIL-22) vector was derived by digesting pED6dpc-2mIL-22 with EcoRI and NotI, and ligating the 1.1 kb mIL-22 cDNA fragment with EcoRI and NotI digested adenovirus vector Adori 1-2. Adori 1-1 green fluorescent protein (GFP) construct was derived by digesting pEGFP-NI (CLONTECH Laboratories, Inc., Palo Alto, Calif.) with EcoR1 and Not1 and inserting the EGFP into the EcoR1 and Not1 site of Adori 1-1. Both constructs were verified by extensive restriction digestion analysis and sequencing of the cDNA inserts within the plasmids. Expression of the mIL-22 cDNA and EGFP are driven from cytomegalovirus (CMV) immediate early promoter and enhancer.

Ad5 E1a deleted (dl327) recombinant adenovirus was generated by homologous recombination in a human kidney embryonic kidney cell line 293. Recombinant adenovirus virus was isolated and subsequently amplified on 293 cells. The virus was released from infected 293 cells by three cycles of freeze thawing. The virus was further purified by two cesium chloride centrifugation gradients and dialyzed against phosphate buffered saline (PBS) pH 7.2 at 4° C. Following dialysis, glycerol was added to a concentration of 10% and the virus was stored at −80° C. until use. The virus was characterized by expression of the transgene, plaque forming units on 293 cells, particles/ml, endotoxin measurements and PCR analysis of the virus and sequence analysis of the IL-22 coding region in the virus.

A single dose of $5\times10^{10}$ particles of recombinant adenovirus encoding mIL-22 was injected into the tail vein of female C57B1/6 mice, age 7-8 weeks. Control mice received an adenovirus encoding GFP or PBS/10% glycerol. Mice from each experimental group were sacrificed at various time points post injection. For hematological and serum chemistry analysis blood was collected by cardiac puncture. Blood was collected via retro-orbital sinus and differential counts were performed on blood smears. Tissue was harvested, fixed in formalin, and stained with hematoxylin and eosin for histopathology.

Example 4

Immunological Effects IL-22

The immunological effects of IL-22 were investigated in a metazoan context by viral introduction of the cDNA of murine IL-22 into mice. An adenoviral vector was used to express a cDNA of murine IL-22 in 8 week old C57/B6 female mice by injection of $5\times10^{10}$ viral particles either intravenously or subcutaneously. Test mice were sacrificed at 7 and 14 days after injection and compared with control mice injected with buffer only or with adenovirus expressing green fluorescent protein (GFP). At days 7 and 14, it was noted that the absolute and relative thymic weights were significantly decreased in the mice that expressed the viral murine IL-22. Absolute mean weight of the spleen was decreased on day 14 and liver weights were slightly increased on day 7. A gross generalized atrophy of the thymus as well as lymphoid depletion (observed microscopically) was apparent on days 7 and 14. An increase in kidney weight as well as enlargement of the liver were also observed.

In addition, there were a number of hematological effects that were apparent on day 7, including decreased red blood cell count, hemoglobin, and hematocrit. These effects, taken together, indicated anemia in the animals. Furthermore, there was an increase in platelets as well as an increase in the white blood cell count due to an increase of neutrophils. In light of these observations there was no evidence of a regenerative response, which indicated that the effects can be at the level of the bone marrow. A possible cause for this is the loss of small molecules through the kidney or gut. Furthermore, there was a slight decrease in Albumin levels at day 7 and day 14 but an increase in serum amyloid A and fibrinogen levels, which are indicative of an acute phase response. Other clinical observations included loss in body weight, signs of minimal dehydrations, increase urine specific gravity, a decrease in urine output and the induction of renal proximal tubular basophilia. The basophilia observed is due to increased cell division and increased rRNA present in the epithelial cells of the renal proximal tube.

Example 5

Preparation and Characterization of Anti-IL-22 Monoclonal and Polyclonal Antibodies Monoclonal and polyclonal antibodies were prepared using routine methodologies also described in the instant specification. The table presented below illustrates the binding and neutralizing specificity of monoclonal antibodies P3/1, P3/2, P3/3 and P3/5 as well as chicken polyclonal antibody that are directed against IL-22.

| IL-22 Antibodies | Rat Monoclonal Abs | | | | Polyclonal Ab Chicken |
|---|---|---|---|---|---|
| | P3/1 | P3/2 | P3/3 | P3/5 | Polyclonal |
| Binding Specificity | Mouse | Human | Mouse/Human | Mouse | Mouse/Human |
| Neutralizing Specificity | Mouse | Human | Mouse/Human | Mouse | Mouse/Human |

Binding specificity was determined by ELISA using mouse or human h/f tagged IL-22 microtiter plates. Each antibody showed strong specificity for either mouse or human IL-22. The neutralizing specificity was determined by assessing the ability of the antibody to inhibit STAT 3 phosphorylation mediated by 5 ng/ml mouse or human h/f tagged IL-22. Enzyme-linked immunosorbant assays (ELISA) using bound murine IL-22 demonstrate that the mAb P3/1 has ~5 nM $ED_{50}$ based on ~2 nM for IL-22-Fc and ~10 nM for H/F IL-22. Moreover, in addition to recognizing recombinant IL-22, P3/1 mAb also binds native IL-22 secreted from T cells that have been transfected with an IL-22 retroviral vector.

The IL-22 antibody P3/1 has been found to have an $ID_{50}$ of ~1 nM, and to work stoichiometricly to block IL-22 activity when the cytokine is present at just saturating conditions (1 nM).

Example 6

Expression of IL-22 mRNA and Receptor

Expression of IL-22 and its receptor was examined semi-quantitative reverse-transcriptase polymerase chain reaction (RT-PCR) in a variety of human and mouse tissues. The experiments reveal that IL-22 messenger RNA (mRNA) is present at very low levels in human testis, lung, prostate and peripheral blood lymphocytes (PBL) as normalized against control actin. Moreover, semi-quantitative RT-PCR shows that IL-22 receptor is detected at highest levels in the human pancreas, and a lower levels in the liver, intestines, skin, thyroid, kidney, heart stomach, testis, salivary glands, adrenal glands and prostate. Alternatively, murine IL-22 receptor shows highest expression in the liver, small intestine, muscle, skin and ovaries, with lower expression in kidney and embryos e8.5 and e19.

Example 7

In Situ Hybridization and Apoptotic Stain for IL-22 Protein

In situ hybridization for IL-22 protein and receptor messenger RNA (mRNA) of mice treated with adenovirus expression IL-22 (AdIL-22) or Lipopolysaccharide (LPS) was performed and the results as follows:

A. Detection of IL-22 Cytokine mRNA

| Tissue | AdIL-22-treated mice | LPS-treated mice |
|---|---|---|
| Liver | Day 1: staining in cytoplasm of hepatocytes slightly positive<br>Days 3 and 14: no specific staining | 6 hrs.: staining in cytoplasm of hepatocytes slightly positive |
| Spleen | Days 1, 3 and 14: slight staining in periarteriolar region | Negative |
| Heart | N/A | Negative |
| Colon | N/A | Negative |
| Kidneys | Day 1: staining in cytoplasm of proximal and distal tubular epithelium, Henle's loop at corticomedullary junction, parietal cells of Bowman space and some epithelial cells was mildly positive<br>Day 4: staining in cytoplasm of proximal and distal tubular epithelium and Henle's loop at corticomedullary junction<br>Day 14: staining in cytoplasm of proximal tubular epithelium | 2 hrs.: staining in cytoplasm of proximal and distal tubular epithelium, Henle's loop at corticomedullary junction was mildly positive<br>6 hrs.: staining in cytoplasm of the proximal and distal tubular epithelium and Henle's loop at the corticomedullary junction, glomerular tuft cells, some parietal cells of the Bowman space and few endothelial cells was slightly to moderately positive |
| Pancreas | N/A | 2 and 6 hrs.: staining in cytoplasm of acinar cells slightly positive |
| Lungs | N/A | 2 and 6 hrs.: staining in pneumocytes type II and/or intraaveolar macrophages was slightly to mildly stained |
| Stomach | N/A | 6 hrs.: staining in cytoplasm of basal chief cells was mild |
| Duodenum and Jejunum | N/A | 2 and 6 hrs.: staining in cytoplasm of enterocyte brush border was moderate to marked and slightly positive in the intestine nervous plexus cells. |

B. Detection of the IL-22 Receptor mRNA in LPS-Treated Mice

| Tissue | LPS-treated mice |
|---|---|
| Liver | 2 and 6 hrs.: staining in the cytoplasm of hepatocytes was slight to mild, nuclear staining was observed in heptocytes, bile duct epithelium and endothelial cells. |
| Kidneys | 2 and 6 hrs.: staining was slight to moderate in the cytoplasm and nucleus of proximal and distal tubular epithelium, Henle's loop at the corticomedullary junction, glomerular tuft cells, some parietal cells of Bowman space and a few endothelial cells. |
| Pancreas | 2 and 6 hrs.: staining in cytoplasm of acinar cells slightly positive |
| Heart | 6 hrs.: nuclear staining was moderately positive in cardiomyocytes and endocardial and endothelial cells. |

IL-22 receptor mRNA is additionally detected in small and large intestine, stomach, lymph nodes, spleen, and lung. Expression of IL-22 receptor can additionally be upregulated by a mediator of an innate immune response, such as LPS.

Finally, TUNEL assays of kidney cells taken from c57BL/6 mice receiving mIL-22 protein intravenously showed a few apoptotic epithelial sells in several proximal convoluted tubules. Mice receiving saline intravenously (control group) demonstrated no positive staining.

These data demonstrate that both the cytokine and receptor can be induced during an innate immune response, and that the induction is restricted to tissues that are in an inflammatory state (LPS). During an adaptive immune response, IL-22 can also be induced from Th1 CD4+ T cells. Since circulating leukocytes do not appear to have the receptor, this result suggests that IL-22 functions as an effector within tissue downstream of an adaptive immune response, as is reinforced by the tissue expression of the receptor, constitutively and further upregulated by an innate inducer of inflammation.

Example 8

IL-22 Mediated Changes in Gene Expression

The ability of IL-22 to modulate levels of gene expression in liver cells of mice infected with an AdIL-22 or Ad-GFP construct was examined.

Frozen mouse livers from day 1 and day 3 post-infection were pulverized and RNA was purified using the Promega RNAgents Total RNA Isolation System (Promega, Madison, Wis.). The RNA was further purified using the RNeasy minikit. Total RNA was isolated from human PBMC's using the RNeasy minikit (Qiagen, Hidden, Germany).

Total RNA was prepared for hybridization by denaturing 10 µg of total RNA for 10 minutes at 70° C. with 100 µM T7/T24-tagged oligo-dT primer (synthesized at Genetics Institute, Cambridge, Mass.), and cooled on ice. First strand cDNA synthesis was performed under the following buffer conditions: 1× first strand buffer (Invitrogen Life Technologies, Carlsbad, Calif.), 10 mM DTT (GIBCO/Invitrogen), 500 µM of each dNTP (Invitrogen Life Technologies, Carlsbad, Calif.)), 400 units of Superscript RT II (Invitrogen Life Technologies) and 40 units RNAse inhibitor (Ambion, Austin, Tex.). The reaction proceeded at 47° C. for 1 hour. Second strand cDNA was synthesized with the addition of the following reagents at the final concentrations listed: 1× second strand buffer (Invitrogen Life Technologies), an additional 200 µM of each dNTP (Invitrogen Life Technologies), 40 units of E. coli DNA polymerase I (Invitrogen Life Technologies), 2 units E. coli RNaseH (Invitrogen Life Technologies), and 10 units of E. coli DNA ligase. The reaction proceeded at 15.80 C for 2 hours. During the last five minutes of the reaction 6 units of T4 DNA polymerase (New England Biolabs, Beverly, Mass.) was added.

The resulting double stranded cDNA was purified with the use of BioMag carboxyl terminated particles as follows: 0.2 mg of BioMag particles (Polysciences Inc., Warrington, Pa.) were equilibrated by washing three times with 0.5M EDTA and resuspended at a concentration of 22.2 mg/ml in 0.5M EDTA. The double stranded cDNA reaction was diluted to a final concentration of 10% PEG/1.25M NaCl, and the bead suspension was added to a final bead concentration of 0.614 mg/ml. The reaction was incubated at room temperature for 10 minutes. The cDNA/bead complexes were washed with 300 µl of 70% ethanol, the ethanol was removed and the tubes were allowed to air dry. The cDNA was eluted with the addition of 20 µl of 10 mM Tris-acetate, pH 7.8, incubated for 2-5 minutes and the cDNA containing supernatate was removed.

10 µl of purified double stranded cDNA was added to an in vitro transcription (IVT) solution which contained, 1×IVT buffer (Ambion, Austin, Tex.) 5,000 units T7 RNA polymerase (Epicentre Technologies, Madison, Wis.), 3 mM GTP, 1.5 mM ATP, 1.2 mM CTP and 1.2 mM UTP (Amersham/Pharmacia,), 0.4 mM each bio-16 UTP and bio-11 CTP (Enzo Diagnostics, Farmingdale, N.Y.), and 80 units RNase inhibitor (Ambion, Austin, Tex.). The reaction proceeded at 37° C. for 16 hours. Labeled RNA was purified with the use of an RNeasy (Qiagen). The RNA yield was quantified by measuring absorbance at 260 nm.

12 µg of the in vitro transcription product was fragmented in 40 mM Tris-actetate, pH 8.0, 100 mM potassium acetate, and 30 mM magnesium acetate for 35 minutes at 94° C. The fragmented, labeled RNA probes were diluted in hybridization buffer at a final composition of 1×2-N-Morpholinoethanesulfonic acid (MES (buffer (pH 6.5), 50 µM Bio948 (control biotinylated oligo that hybridizes to landmark features on the probe array (Genetics Institute, Cambridge, Mass.), 100 µg/ml herring sperm DNA (Promega, Madison, Wis.), 500 µg/ml acetylated BSA (Invitrogen Life Technologies) and 1 µl/µg standard curve reagent (Proprietary reagent supplied by Gene Logic, Gaithersburg, Md.). This hybridization solution was pre-hybridized with two glass beads (Fisher Scientific, Pittsburgh, Pa.) at 45° C. overnight. The hybridization solution was removed to a clean tube and heated for 1-2 min at 95° C. and microcentrifuged on high for 2 minutes to pellet insoluble debris. Oligonucleotide array cartridges (Murine 74 Kv2, Affymetrix, Santa Clara, Calif.) were prewet with non-stringent wash buffer (0.9M NaCl, 60 mM sodium phosphate, 6 mM EDTA and 0.01% Tween20) and incubated at 45° C. with rotation for 5-10 minutes. Buffer was removed from the cartridges, and the arrays were hybridized with 180 ul of the hybridization solution at 45° C. rotating at 45-60 rpm overnight. After overnight incubation the hybridization solutions were removed and the cartridges were filled with non-stringent wash buffer. The array cartridges were washed using a fluidics station according with 10 cycles of 2 mixes/cycle non-stringent wash buffer at 25° C. followed by 4 cycles of 15 mixes/cycle stringent wash buffer (100 mM MES, 0.1M Na$^+$, 0.01% Tween20 and 0.005% antifoam). The probe array was then first stained for 10 minutes at 25° C. in SAPE solution (100 mM MES, 1M Na$^+$; 0.05% Tween20, 0.005% antifoam, 2 mg/ml acetylated BSA (Invitrogen Life Technologies) and 10 ug/ml R phycoerythrin streptavidin (Molecular. Probes, Eugene, Oreg.)). After first staining the probe array was washed for 10 cycles of 4 mixes/cycle with non-stringent wash buffer at 25° C. The probe array was then stained for 10 minutes at 25° C. in antibody solution (100 mM MES, 1M Na$^+$, 0.05% Tween20, 0.005% antifoam, 2 mg/ml acetylated BSA (Invitrogen Life Technologies), 100 µg/ml Goat IgG (SIGMA, St. Louis, Mo.) and 3 µg/ml biotinylated anti-streptavidin antibody (goat) (Vector Laboratories,). Following the second stain the probe array was stained again for an additional 10 minutes at 25° C. in SAFE solution. Finally, the probe array was washed for 15 cycles of 4 mixes/cycle with non-stringent wash buffer at 30° C.

Arrays were scanned using an Affymetrix gene chip scanner (Affymetrix, Santa Clara, Calif.). The scanner contained a scanning confocal microscope and used an argon ion laser for the excitation source and emission is detected by a photomultiplier tube at 530 nm bandpass filter (fluorscein 0 or 560 longpass filter (phycoerythrin).

mRNA were analyzed on the Murine 74 k (Mu74K) chip set. The data was reduced with the use of GENECHIP 4.0 software. Each experimental sample was compared to a time matched control in a two-file analysis. The data were filtered with the criteria for genes that were called "Present" in one group, and removing all genes that were not called either "Increasing" or "Decreasing".

Data for three mice are presented below (AD-GIL-19 Mouse 49, 51, and 52). Shown are genes whose expression changed relative to Ad-GFP control, with the indicated average-fold change shown for each animal. The changes observed in gene expression of Ad-IL-22 treated animals are consistent with the induction by IL-22 of an acute phase response. The observed changes are also indicative of an inflammatory state in the treated animal.

| | | Day 3 Livers—U74v2 | | |
|---|---|---|---|---|
| | | Ad-GIL-19 | Ad-GIL-19 | Ad-GIL-19 |
| | | mouse number | | |
| | | Mouse 49 | Mouse 51 | Mouse 52 |
| | | Avg Fold | Avg Fold | Avg Fold |
| Identifier | Gene Name | Change | Change | Change |
| 1300017C10RIK | RIKEN cDNA 1300017C10 gene | 23.4 | 17.2 | 19.3 |
| SAA-PS | serum amyloid A, pseudogene | 24.6 | 13.9 | 24.3 |
| SAA1 | serum amyloid A 1 | 11.9 | 9.7 | 12.3 |
| SAA2 | serum amyloid A 2 | 10.0 | 8.9 | 10.3 |
| PRTN3 | proteinase 3 | 15.2 | 14.3 | 17.1 |
| SPP1 | secreted phosphoprotein 1 | 10.2 | 7.8 | 10.7 |
| LCN2 | lipocalin 2 | 13.4 | 10.3 | 13.3 |
| SAA3 | serum amyloid A 3 | 10.5 | 5.4 | 8.2 |
| GRO1 | GRO1 oncogene | 8.2 | 5.6 | 7.2 |
| LY6D | lymphocyte antigen 6 complex, locus D | 6.0 | 5.5 | 4.9 |
| GRO1 | GRO1 oncogene | 7.0 | 5.6 | 7.2 |
| RAD51L1 | RAD51 like 1 (*S. cerevisiae*) | 4.4 | 3.7 | 3.8 |
| GAS6 | growth arrest specific 6 | 4.1 | 3.5 | 4.8 |
| SPI2-2 | serine protease inhibitor 2-2 | 3.7 | 2.8 | 3.8 |
| GADD45G | growth arrest and DNA-damage-inducible 45 gamma | 3.9 | 2.7 | 3.4 |
| CEBPD | CCAAT/enhancer binding protein (C/EBP), delta | 5.3 | 3.2 | 3.9 |
| TNFRSF1A | tumor necrosis factor receptor superfamily, member 1a | 3.6 | 2.6 | 3.0 |
| CISH3 | cytokine inducible SH2-containing protein 3 | 4.0 | 3.8 | |

-continued

Day 3 Livers—U74v2

| | | Ad-GIL-19 Mouse 49 Avg Fold Change | Ad-GIL-19 Mouse 51 Avg Fold Change | Ad-GIL-19 Mouse 52 Avg Fold Change |
|---|---|---|---|---|
| Identifier | Gene Name | | | |
| IL1R1 | interleukin 1 receptor, type I | 5.2 | 2.6 | 5.6 |
| SAP | serum amyloid P-component | 3.1 | 2.5 | 3.3 |
| PEX11A | peroxisomal biogenesis factor 11a | 4.2 | | 3.2 |
| 2310031E04RIK | EST | 2.9 | 2.7 | 3.3 |
| AA880891 | EST | 2.7 | 2.4 | 2.8 |
| CD14 | CD14 antigen | 3.4 | 2.3 | 2.6 |
| MT1 | metallothionein 1 | 2.7 | 2.4 | 2.9 |
| UNK_AW124835 | EST | 2.2 | | 2.0 |
| TM4SF7 | transmembrane 4 superfamily member 7 | 2.6 | 2.8 | 2.4 |
| DNCLC1 | dynein, cytoplasmic, light chain 1 | 2.5 | 2.4 | 2.6 |
| SAA4 | serum amyloid A 4 | 3.2 | | 2.8 |
| 2410006H10RIK | RIKEN cDNA 2410006H10 gene | 2.2 | 2.1 | 2.0 |
| RBM3 | RNA binding motif protein 3 | 2.7 | 2.8 | 2.8 |
| 1300003D03RIK | RIKEN cDNA 1300003D03 gene | 2.2 | | 2.4 |
| CEBPB | CCAAT/enhancer binding protein (C/EBP), beta | 2.0 | | 2.3 |
| MT2 | metallothionein 2 | 2.2 | 2.1 | 2.3 |
| ORM2 | orosomucoid 2 | 1.7 | 1.7 | 2.0 |
| VNN1 | vanin 1 | 2.0 | 2.1 | |
| GTF2A2 | general transcription factor IIa, 2 (12kD subunit) | 2.2 | | 2.4 |
| ITIH4 | inter alpha-trypsin inhibitor, heavy chain 4 | 1.8 | | 1.9 |
| ITIH3 | inter-alpha trypsin inhibitor, heavy chain 3 | 1.8 | 1.7 | 1.9 |
| NPN3 | neoplastic progression 3 | 2.2 | | 2.5 |
| U62673 | EST | −2.4 | −3.2 | |
| PAPSS2 | 3'-phosphoadenosine 5'-phosphosulfate synthase 2 | −2.0 | −2.3 | |
| TEMT | thioether S-methyltransferase | −2.2 | | −1.7 |
| TTR | transthyretin | −2.0 | −1.8 | |
| CBG | corticosteroid binding globulin | −3.4 | −2.8 | −2.8 |
| HSD11B1 | hydroxysteroid 11-beta dehydrogenase 1 | −2.1 | −1.9 | |
| LIFR | leukemia inhibitory factor receptor | −2.5 | −2.0 | −1.7 |
| LIFR | leukemia inhibitory factor receptor | −2.5 | −2.0 | −1.7 |
| HPGD | hydroxyprostaglandin dehydrogenase 15 (NAD) | −1.9 | −2.5 | |
| CBG | corticosteroid binding globulin | −3.5 | −2.8 | −2.8 |
| HAL | histidine ammonia lyase | −2.2 | −2.0 | −2.1 |
| CYP2F2 | cytochrome P450, 2f2 | −2.5 | −2.3 | −1.7 |
| KEG1 | kidney expressed gene 1 | −2.9 | −2.2 | |
| AI266885 | EST | −4.7 | −3.1 | −2.4 |
| Called Present in only one animal | | | | |
| PAP | pancreatitis-associated protein | 9.2 | | |
| 1300007C21RIK | RIKEN cDNA 1300007C21 gene | 4.7 | | |
| REG2 | rat regenerating islet-derived, mouse homolog 2 | 9.8 | | |
| UNK_AE000664 | EST | 9.6 | | |
| SERINE/THREONINE-PROTEIN KI... | SERINE/THREONINE-PROTEIN KI. | 2.1 | | |
| 1300007C21RIK | RIKEN cDNA 1300007C21 gene | 3.8 | | |
| CRAT | carnitine acetyltransferase | 2.6 | | |
| AS2 | arylsulfatase A | 3.2 | | |
| 2310009M24RIK | RIKEN cDNA 2310009M24 gene | 2.0 | | |
| 2310004B05RIK | RIKEN cDNA 2310004B05 gene | 2.8 | | |
| REG1 | rat regenerating islet-derived, mouse homolog 1 | 2.3 | | |
| AW048468 | esterase 31 | 1.8 | | |
| PAP | pancreatitis-associated protein | 7.7 | | |
| SULT-X1 | sulfotransferase-related protein SULT-X1 | −2.6 | | |
| ES31 | esterase 31 | −1.8 | | |
| AW538652 | EST | | −1.9 | |
| GAMT | guanidinoacetate methyltransferase | −2.0 | | |
| SC5D | sterol-C5-desaturase (fungal ERG3, delta-5-desaturase) homolog (S. cerevisae) | | −1.9 | |
| GHR | growth hormone receptor | | −3.0 | |
| AI839995 | EST | −1.8 | | |
| 0610025L15RIK | RIKEN cDNA 0610025L15 gene | | −1.9 | |
| AGXT | alanine-glyoxylate aminotransferases | −2.5 | | |
| PAH | phenylalanine hydroxylase | −2.0 | | |
| IGFBP2 | insulin-like growth factor binding protein 2 | −2.5 | | |
| AI647632 | EST | −2.1 | | |
| AI647632 | EST | −2.1 | | |
| G6PC | glucose-6-phosphatase, catalytic | −2.2 | | |
| CYP17 | cytochrome P450, 17 | | −3.0 | |
| GSTA2 | glutathione S-transferase, alpha 2 (Yc2) | −2.3 | | |
| CYP26 | cytochrome P450, 26, retinoic acid | −9.0 | | |
| THRSP | thyroid hormone responsive SPOT14 homolog (Rattus) | −2.7 | | |
| FMO3 | flavin containing monooxygenase 3 | −2.6 | | |

Example 9

Effect of an Anti-IL-22 Antibody in an In Vivo Arthritis Model

The ability of the P3/1 monoclonal antibody to ameliorate symptoms in a collagen-induce arthritis (CIA) murine model was examined. Male DBA/1 (Jackson Laboratories, Bar Harbor, Me.) mice were used for all experiments. Antibody was administered prophylactically or therapeutically to DBA mice. In the therapeutic regimen, treatment was initiated if disease was observed for two consecutive days in a mouse.

Arthritis was induced with the use of bovine collagen type II (Chondrex, Redmond, Wash.). Bovine collagen type II (Chondrex, Redmond, Wash.) was dissolved in 0.1 M acetic acid and emulsified in an equal volume of CFA (Sigma) containing 1 mg/ml *Mycobacterium tuberculosis* (strain H37RA). 100 µg of bovine collagen was injected subcutaneously in the base of the tail on day 0. On day 21, mice were injected subcutaneously, in the base of the tail, with a solution containing 200 µg of bovine collagen in 0.1M acetic acid that had been mixed with an equal volume of Incomplete Freund's adjuvant (Sigma). Naïve animals received the same sets of injections, minus collagen. The dosing protocol is shown schematically in FIG. 1.

Mice were monitored at least three times a week for disease progression. Individual limbs were assigned a clinical score based on the index: 0=normal; P=prearthritic, characterized by focal erythema on the tips of digits; 1=visible erythema accompanied by 1-2 swollen digits; 2=pronounced erythema, characterized by paw swelling and/or multi digit swelling; 3=massive swelling extending into ankle or wrist joint; 4=difficulty in use of limb or joint rigidity. Thus, the sum of all limb scores for any given mouse yielded a maximum total body score of 16.

At various stages of disease, animals were euthanized, tissues were harvested and paws were fixed in 10% formalin for histology or 4% paraformaldeyde, pH 7.47, decalcified in 20% EDTA (pH 8.0) and embedded in paraffin for in situ hybridization. Using light microscopy the paws were scored on a 5-grade scoring method (0-4) to characterize the intensity and extent of arthritis. Inflammatory infiltrates were used for scoring in addition to other changes related to the inflammation, such as pannus formation, fibrous of the synovial membrane, articular cartilage erosin and/or subchondral bone destruction. Hisotology grades were determined using readings of individual paws: NAD=0 or nothing abnormal discovered; 1=Slight to moderate; 2: Mild to moderate; 3: Marked and 4: Massive.

Figure 2:
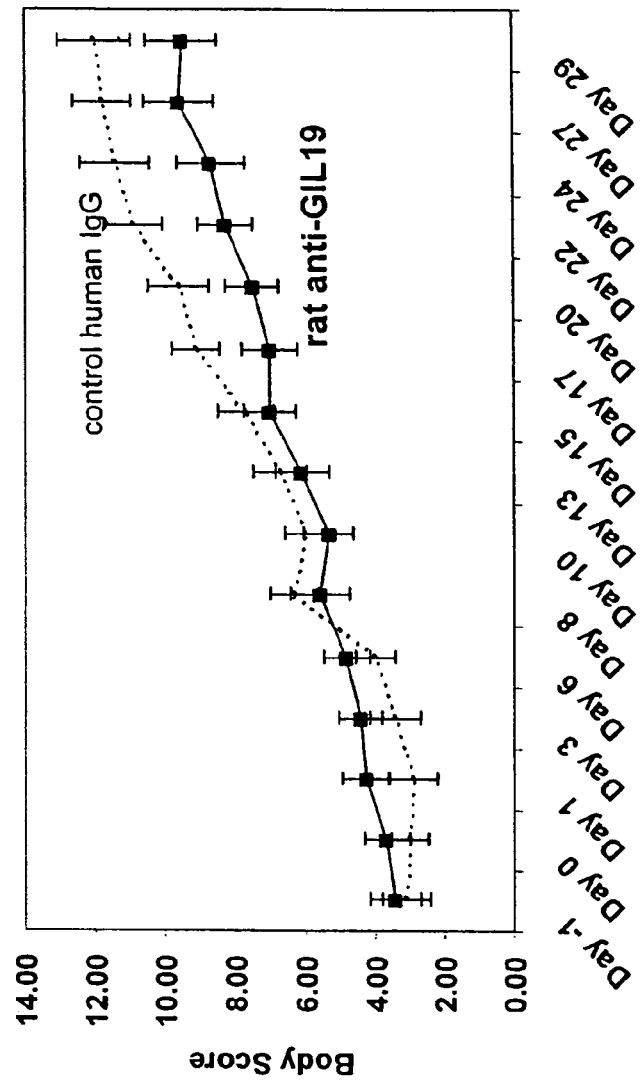
FIG. 2 is a graph showing body score following treatment of arthritic mice with IL-22 antibody or control using a therapeutic treatment regimen.

The effect of the therapeutic administration of IL-22 antibody is shown in FIG. 2. Body score is shown as a function of time. Mice administered anti-IL-22 antibody showed significantly decreased symptoms relative to mice administered control human IgG or PBS (data not shown).

Figure 3:
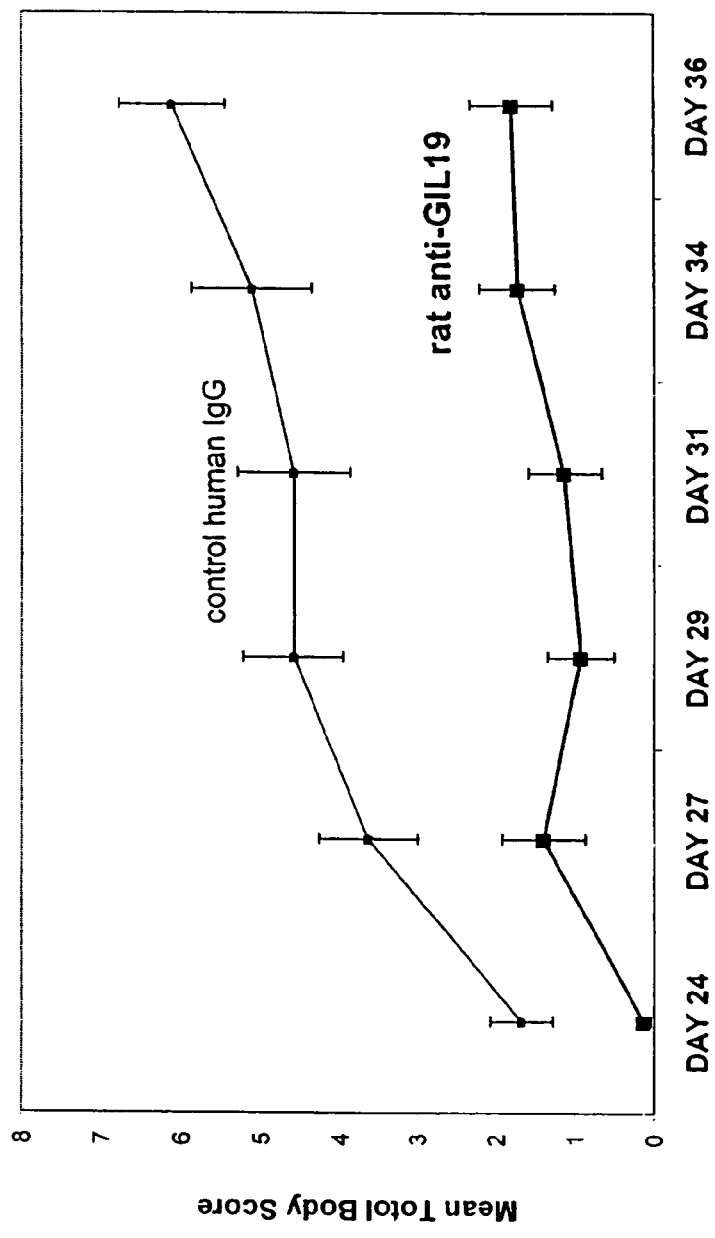
FIG. 3 is a graph showing body score following treatment of arthritic mice with IL-22 antibody or control using a prophylactic treatment regimen.
Figure 4:
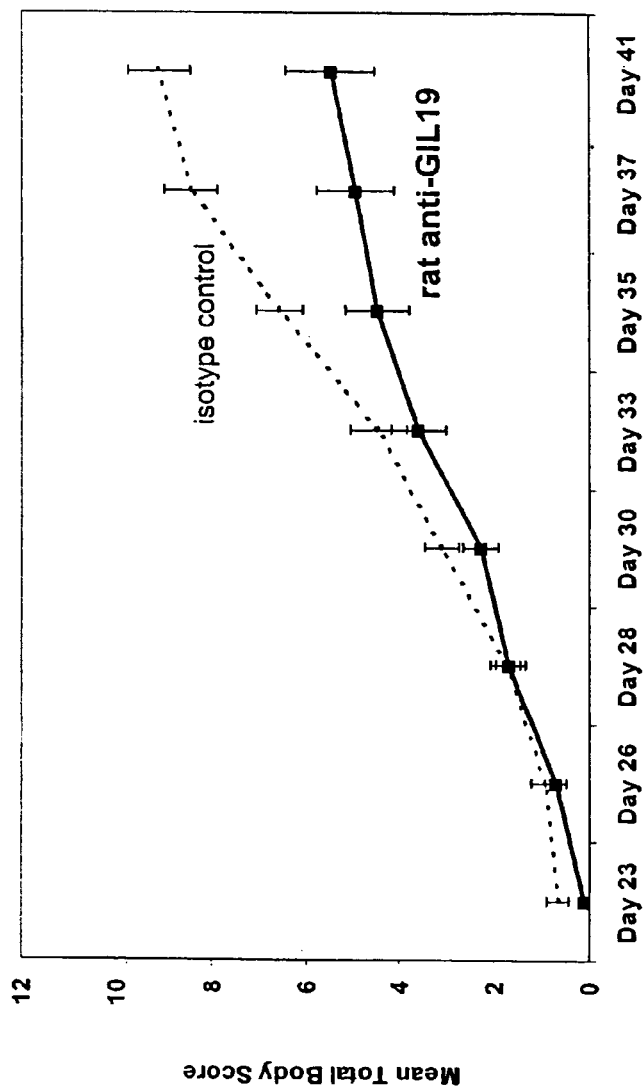
FIG. 4 is a graph showing body score following treatment of severely arthritic mice with IL-22 antibody or control.
Figure 5:
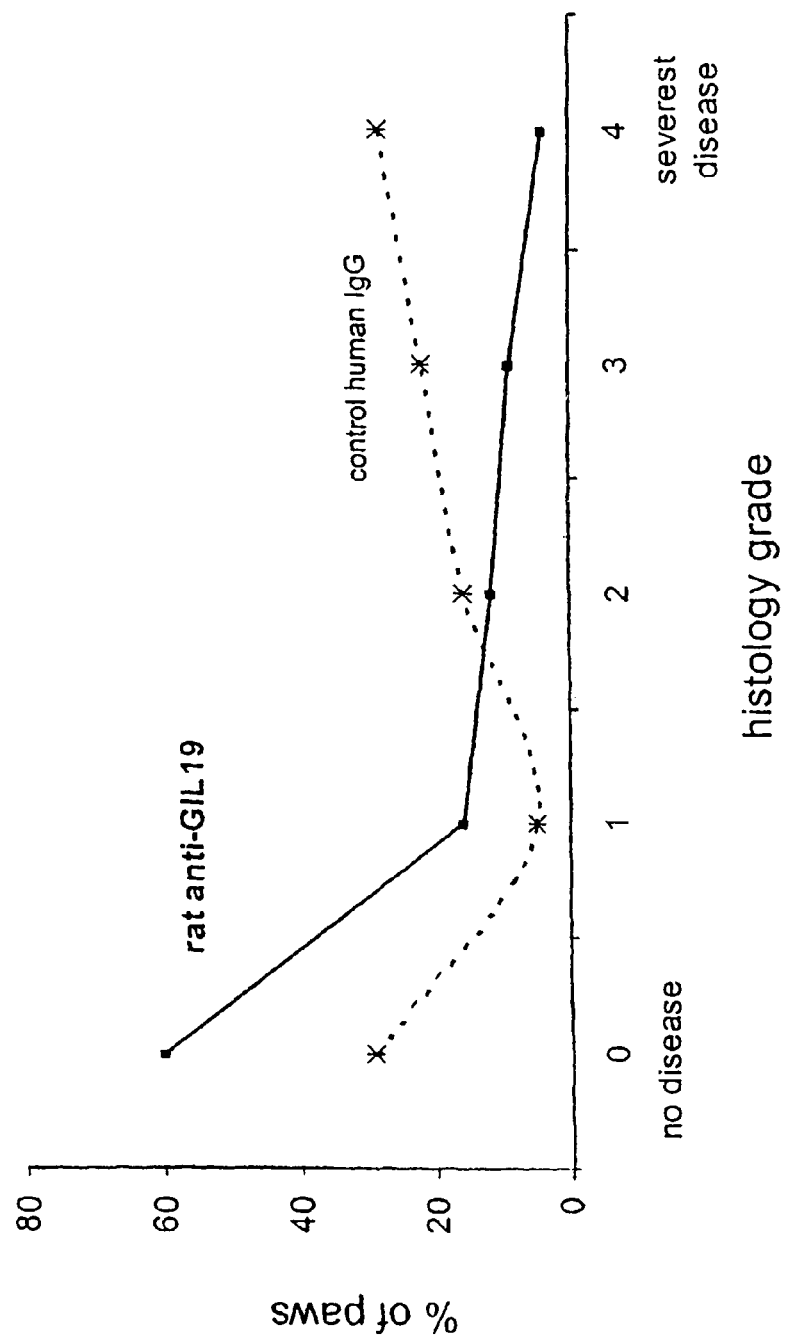
FIG. 5 is graph showing relative percentages of paws showing a given histology grade following with IL-22 antibody or control.

The effect of prophylactic administration of neutralizing IL-22 antibody is shown in FIGS. 3-5. Body score is shown as a function of time following administration of anti-IL-22 or control antibody. Mice administered anti-IL-22 antibody showed significantly decreased symptoms relative to mice administered control rat IgG or PBS (data not shown).

Body score was also examined in mice subjected to a separate prophylactic regimen. The results are shown in FIG. 4 as a function of time. Mice treated with control antibody demonstrated a significantly higher mean total body score than mice treated with anti-IL-22. Ice administered anti-IL-22 antibody showed significantly decreased symptoms relative to mice administered control rat IgG1 or PBS (data not shown).

The progression of disease in paws of mice subjected to the prophylactic regimen is shown in FIG. 5. Mice at day 36 were sacrificed, and the severity of disease in their paws examined. The paws were assigned a histology grade of 0 to 4, with 0 corresponding to no disease and 4 representing most severe disease. For rats injected with IL-22 antibody, over 60% had a histology grade of "0", while about 20% of the mice had a histology grade of "1". About 15% of the mice showed a histology grade of "2", and about 10% of the mice showed a histology grade of "3". A small percentage of mice showed a histology grade of "4". For mice injected with control antibody, about 30% showed a histology grade of "0", and about 5% of the mice showed a histology grade of "1". The remaining mice exhibited more severe pathology grades: about 18% showed a histology grade of "2", while 20% showed a pathology grade of "3", and the remaining mice showed a histology grade of "4". Mice administered anti-IL-22 antibody showed significantly decreased symptoms relative to mice administered control rat IgG1 or PBS (data not shown).

These results demonstrate that administration of IL-22 antibody either prophylactically or therapeutically significantly ameliorates symptoms of arthritis in an animal system.

Example 10

In Situ Hybridization of IL-22 Transcripts

The expression of IL-22 and IL-22 receptor sequences in various cell types of foot pads of arthritic mice was determined. Anti-sense IL-22 and IL-22 murine receptor riboprobes were produced by generating 2 independent PCR products from the corresponding transcripts. The oligonucleotides 5'-GACTGATAATACGACTCACTATAGGGC-GAACAATTTTGACTCCGATATTGTC CAAG-3' (SEQ ID NO:6) and 5'-AGGATGGAGACATCTGACTGCCCTACG-3' (SEQ ID NO:5) were used to generate for a IL-22 receptor sense probe and 5'-ACAATTTTGACTCCGATATTGTC-CAAG (SEQ ID NO:7) and 3'-GACTGATAATACGACT-CACTATAGGGCGAAGGATGGAGACATCTGACTGCC CTACG-3' (SEQ ID NO:8) were used to generate for a IL-22 receptor antisense probe. Following PCR amplification probes were generated using T7 RNA polymerase and in vitro transcription.

A probe for IL-22 sequences was constructed by placing the following sequence in a plasmid and placing the sequence under the control of T7 and SP6 promoters to produce sense or anti-sense transcripts:
CAGCCATACATCGTCAACCGCACCTT-TATGCTGGCCAAGGAGGCCAGCCTTGCA-GATAACAACACAGATGT CCGGCTCATCGGG-GAGAAACTGTTCCGAGGAGTCAGTGCTAAGGATCA GTGCTACCTGATGAAGCAGGTGC TCAACTTCAC-CCTGGAAGACGTTCTGCTCCCCCAGTCA-GACAGGTTCCA (SEQ ID NO:9)

T7 RNA polymerase binding sites were incorporated into the oligonucleotides to insert T7 binding sites at either the 5' end of the PCR product for sense riboprobe or the 3' end of the PCR product for antisense riboprobe. Digoxygenin labeled probes were prepared with the use of a DIG RNA labeling mix (Roche Diagnostics, Mannheim, Germany), as described by the manufacturer, and T7 RNA polymerase (Roche Diagnostics). IL-22 receptor mRNA-positive cells in the paw of CIA murine model were macrophages, fibroblasts, a subpopulation of lymphocytes, activated osteoblasts, synoviocytes and epidermis. No positive staining was seen in the control paws or with sense probes. mIL-22 mRNA positive cells were: neutrophils, macrophages, fibroblasts and Osteocytes. No staining was seen in the paw section treated with the sense probe and the control mouse paw stained with mIL-22 mRNA. In situ hybridization showed the presence of both the IL-22 receptor and cytokine in the paws of arthritic mice.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating psoriasis in a subject comprising administering to the subject an antibody or antigen-binding fragment thereof that binds to interleukin-22 (IL-22) in an amount sufficient to treat the psoriasis in the subject.

2. The method of claim 1, wherein said IL-22 comprises the amino acid sequence of amino acids 34-179 of SEQ ID NO:2.

3. The method of claim 2, wherein the subject is a human.

4. The method of claim 1, wherein said IL-22 comprises the amino acid sequence of SEQ ID NO:2.

5. The method of claim 1, wherein said antibody, or antigen-binding fragment thereof, binds to a fragment of IL-22 comprising an amino acid sequence selected from the group consisting of amino acids 50-60, 63-81, 84-93, and 168-177 of SEQ ID NO:2.

6. The method of claim 1, wherein said antibody, or antigen-binding fragment thereof, is selected from the group consisting of a monoclonal antibody, a polyclonal antibody, a chimeric antibody, a single-chain antibody, a CDR-grafted antibody, and a humanized antibody.

7. The method of claim 6, wherein said antibody, or antigen-binding fragment thereof, is a monoclonal antibody.

8. The method of claim 1, wherein said antibody, or antigen-binding fragment thereof, is a human antibody.

9. The method of claim 1, wherein said subject is a human.

10. The method of claim 1, wherein said antibody, or antigen-binding fragment thereof, neutralizes IL-22 binding with an $ED_{50}$ of about 5 nM detected by an enzyme-linked immunoabsorbent assay (ELISA).

11. The method of claim 1, wherein said antibody or antigen-binding fragment thereof is administered subcutaneously or intravenously.

12. A method of ameliorating symptoms associated with psoriasis, comprising administering to a subject antibody or antigen-binding fragment thereof that binds to IL-22 in an amount sufficient to ameliorate the symptoms in the subject.

13. The method of claim 12, wherein said IL-22 antibody, or antigen-binding fragment thereof, is administered therapeutically.

14. The method of claim 12, wherein said IL-22 antibody, or antigen-binding fragment thereof, is administered prophylactically.

15. The method of claim 12, wherein said antibody, or antigen-binding fragment thereof, neutralizes IL-22 binding with an $ED_{50}$ of about 5 nM detected by an enzyme-linked immunoabsorbent assay (ELISA).

16. The method of claim 12, wherein said subject is a human.

17. The method of claim 12, wherein said IL-22 comprises the amino acid sequence of amino acids 34-179 of SEQ ID NO:2.

18. The method of claim 17, wherein the subject is a human.

19. The method of claim 12, wherein said IL-22 comprises the amino acid sequence of SEQ ID NO:2.

20. The method of claim 12, wherein said antibody, or antigen-binding fragment thereof, binds to a fragment of IL-22 comprising an amino acid sequence selected from the group consisting of amino acids 50-60, 63-81, 84-93, and 168-177 of SEQ ID NO:2.

21. The method of claim 12, wherein said antibody, or antigen-binding fragment thereof, is selected from the group consisting of a monoclonal antibody, a polyclonal antibody, a chimeric antibody, a single-chain antibody, a CDR-grafted antibody, and a humanized antibody.

22. The method of claim 21, wherein said antibody, or antigen-binding fragment thereof, is a monoclonal antibody.

23. The method of claim 12, wherein said antibody, or antigen-binding fragment thereof, is a human antibody.

24. The method of claim 12, wherein said antibody or antigen-binding fragment thereof is administered subcutaneously or intravenously.

* * * * *